(12) United States Patent
Kuhr et al.

(10) Patent No.: US 9,173,608 B2
(45) Date of Patent: Nov. 3, 2015

(54) SPACE-SAVING MAGAZINING OF ANALYTICAL AIDS

(71) Applicant: Roche Diagnostics Operations, Inc., Indianapolis, IN (US)

(72) Inventors: Hans-Juergen Kuhr, Mannheim (DE); Hans List, Hesseneck-Kailbach (DE); Wilhelm Leichner, Mannheim (DE); Uwe Kraemer, Ilvesheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 0 days.

(21) Appl. No.: 13/895,172

(22) Filed: May 15, 2013

(65) Prior Publication Data

US 2013/0324807 A1 Dec. 5, 2013

Related U.S. Application Data

(63) Continuation of application No. 13/212,699, filed on Aug. 18, 2011, now abandoned, which is a continuation of application No. PCT/EP2010/000865, filed on Feb. 12, 2010.

(30) Foreign Application Priority Data

Feb. 19, 2009 (EP) ..................................... 09153211
Aug. 20, 2009 (EP) ..................................... 09168335

(51) Int. Cl.
*A61B 5/151* (2006.01)
*A61B 5/15* (2006.01)
(Continued)

(52) U.S. Cl.
CPC ........... *A61B 5/15161* (2013.01); *A61B 5/1411* (2013.01); *A61B 5/1451* (2013.01);
(Continued)

(58) Field of Classification Search
CPC ....................................... A61B 5/151–5/15198
USPC ................................... 606/181–183; 600/583
See application file for complete search history.

(56) References Cited

U.S. PATENT DOCUMENTS

| 5,443,080 A | 8/1995 | D'Angelo et al. |
| 6,036,924 A | 3/2000 | Simons et al. |

(Continued)

FOREIGN PATENT DOCUMENTS

| DE | 19819407 A1 | 11/1999 |
| EP | 1360932 A1 | 11/2003 |

(Continued)

OTHER PUBLICATIONS

Banauch et al., A glucose dehydrogenase for glucose determination in body fluids, Z. Klin. Chem. KLin. Biochem, vol. 13, 1975, pp. 101-107.

(Continued)

*Primary Examiner* — Sean Dougherty
*Assistant Examiner* — Michael C Stout
(74) *Attorney, Agent, or Firm* — Harness, Dickey

(57) ABSTRACT

An analytical magazine is proposed, which comprises a plurality of analytical aids accommodated in chambers. The analytical magazine is arranged to be accommodated in at least two orientations in an analytical system. The analytical magazine is furthermore arranged to provide the analytical system, in the orientations, in each case with a plurality of analytical aids. At least one sampling movement can be executed by means of the analytical aids. The analytical magazine is arranged to make a remagazining of the analytical aids possible.

6 Claims, 5 Drawing Sheets

(51) Int. Cl.
- *G01N 33/487* (2006.01)
- *A61B 5/145* (2006.01)
- *A61B 5/1455* (2006.01)
- *A61B 5/1468* (2006.01)
- *A61B 5/157* (2006.01)
- *A61B 10/00* (2006.01)

(52) U.S. Cl.
CPC ............ *A61B5/1455* (2013.01); *A61B 5/1468* (2013.01); *A61B 5/157* (2013.01); *A61B 5/15151* (2013.01); *A61B 10/007* (2013.01); *G01N 33/4875* (2013.01)

(56) References Cited

U.S. PATENT DOCUMENTS

| | | | |
|---|---|---|---|
| 6,251,083 | B1 | 6/2001 | Yum et al. |
| 7,288,073 | B2 | 10/2007 | Effenhauser et al. |
| 7,553,615 | B2 | 6/2009 | Heindl et al. |
| 7,892,185 | B2* | 2/2011 | Freeman et al. ............ 600/583 |
| 7,959,581 | B2 | 6/2011 | Calasso et al. |
| 8,234,767 | B2* | 8/2012 | Roeper et al. ................ 29/418 |
| 8,303,518 | B2* | 11/2012 | Aceti et al. ................ 600/583 |
| 2002/0087056 | A1* | 7/2002 | Aceti et al. ................ 600/309 |
| 2002/0120216 | A1* | 8/2002 | Fritz et al. ................ 600/583 |
| 2002/0188224 | A1 | 12/2002 | Roe et al. |
| 2003/0191415 | A1 | 10/2003 | Moerman et al. |
| 2003/0199909 | A1 | 10/2003 | Boecker et al. |
| 2003/0212347 | A1 | 11/2003 | Sohrab |
| 2003/0212423 | A1 | 11/2003 | Pugh et al. |
| 2004/0034318 | A1 | 2/2004 | Fritz et al. |
| 2004/0092842 | A1 | 5/2004 | Boecker et al. |
| 2004/0098009 | A1* | 5/2004 | Boecker et al. ............ 606/181 |
| 2004/0102803 | A1* | 5/2004 | Boecker et al. ............ 606/183 |
| 2005/0027211 | A1 | 2/2005 | Kuhr et al. |
| 2005/0033340 | A1* | 2/2005 | Lipoma et al. ............ 606/181 |
| 2005/0214891 | A1 | 9/2005 | Horn et al. |
| 2006/0008389 | A1* | 1/2006 | Sacherer et al. ............ 422/102 |
| 2006/0161078 | A1* | 7/2006 | Schraga ........................ 600/583 |
| 2006/0178600 | A1 | 8/2006 | Kennedy et al. |
| 2006/0184064 | A1 | 8/2006 | Paasch et al. |
| 2006/0200044 | A1* | 9/2006 | Freeman et al. ............ 600/583 |
| 2006/0231442 | A1* | 10/2006 | Windus-Smith et al. ..... 206/438 |
| 2006/0264996 | A1 | 11/2006 | LeVaughn et al. |
| 2007/0016103 | A1* | 1/2007 | Calasso et al. ............ 600/583 |
| 2007/0100255 | A1* | 5/2007 | Boecker et al. ............ 600/583 |
| 2007/0129650 | A1 | 6/2007 | Freeman et al. |
| 2007/0142748 | A1* | 6/2007 | Deshmukh et al. ........... 600/583 |
| 2007/0142854 | A1 | 6/2007 | Schraga |
| 2007/0167872 | A1 | 7/2007 | Freeman et al. |
| 2007/0173741 | A1* | 7/2007 | Deshmukh et al. ........... 600/583 |
| 2007/0219574 | A1* | 9/2007 | Freeman et al. ............ 606/185 |
| 2007/0255301 | A1* | 11/2007 | Freeman et al. ............ 606/181 |
| 2007/0292314 | A1 | 12/2007 | Effenhauser et al. |
| 2008/0021346 | A1 | 1/2008 | Haar et al. |
| 2008/0039887 | A1* | 2/2008 | Conway et al. ............ 606/182 |
| 2008/0040919 | A1 | 2/2008 | Griss et al. |
| 2008/0094804 | A1 | 4/2008 | Reynolds et al. |
| 2008/0103415 | A1 | 5/2008 | Roe et al. |
| 2008/0213809 | A1* | 9/2008 | Heindl et al. ................ 435/14 |
| 2008/0243032 | A1 | 10/2008 | Hindelang et al. |
| 2008/0294068 | A1* | 11/2008 | Briggs et al. ................ 600/583 |
| 2008/0300509 | A1* | 12/2008 | Hoenes et al. ................ 600/583 |
| 2009/0010802 | A1 | 1/2009 | Joseph et al. |
| 2009/0093695 | A1 | 4/2009 | Nakamura et al. |
| 2009/0099477 | A1 | 4/2009 | Hoenes et al. |
| 2009/0099585 | A1* | 4/2009 | Conway et al. ............ 606/182 |
| 2009/0192411 | A1* | 7/2009 | Freeman ........................ 600/583 |
| 2009/0204025 | A1* | 8/2009 | Marsot et al. ................ 600/573 |
| 2010/0010375 | A1 | 1/2010 | Haar et al. |
| 2010/0185120 | A1* | 7/2010 | Sacherer et al. ............ 600/583 |
| 2010/0222799 | A1* | 9/2010 | Roeper et al. ................ 606/181 |
| 2010/0234869 | A1* | 9/2010 | Sacherer ........................ 606/182 |
| 2011/0125059 | A1* | 5/2011 | Petrich et al. ................ 600/583 |
| 2011/0143416 | A1 | 6/2011 | Horn et al. |
| 2012/0039772 | A1 | 2/2012 | Hoenes |
| 2012/0041339 | A1 | 2/2012 | Kuhr et al. |
| 2012/0063970 | A1 | 3/2012 | List et al. |

FOREIGN PATENT DOCUMENTS

| | | |
|---|---|---|
| EP | 1360935 A1 | 11/2003 |
| EP | 1900321 A1 | 3/2008 |
| EP | 1929937 A1 | 6/2008 |
| EP | 1997429 A1 | 12/2008 |
| EP | 2042098 A1 | 4/2009 |
| EP | 2050392 A1 | 4/2009 |
| WO | 0164105 A1 | 9/2001 |
| WO | 2002101343 A2 | 12/2002 |
| WO | 03070099 A1 | 8/2003 |
| WO | 2003088834 A1 | 10/2003 |
| WO | 2005065414 A2 | 7/2005 |
| WO | 2005104948 A1 | 11/2005 |
| WO | 2006031920 A2 | 3/2006 |
| WO | 2007001003 A1 | 1/2007 |
| WO | 2008145625 A2 | 12/2008 |
| WO | 2009036986 A2 | 3/2009 |

OTHER PUBLICATIONS

Bergmeyer, Methoden der enzymatischen Analyse (Methods of enzymatic analysis), Verlag Chemie, 2nd edition, 1970, p. 417.

Hoenes et al., The Technology Behind Glucose Meters: Test Strips, Diabetes Technology & Therapeutics, vol. 10, Supplement 1, 2008, pp. S-10-S26.

* cited by examiner

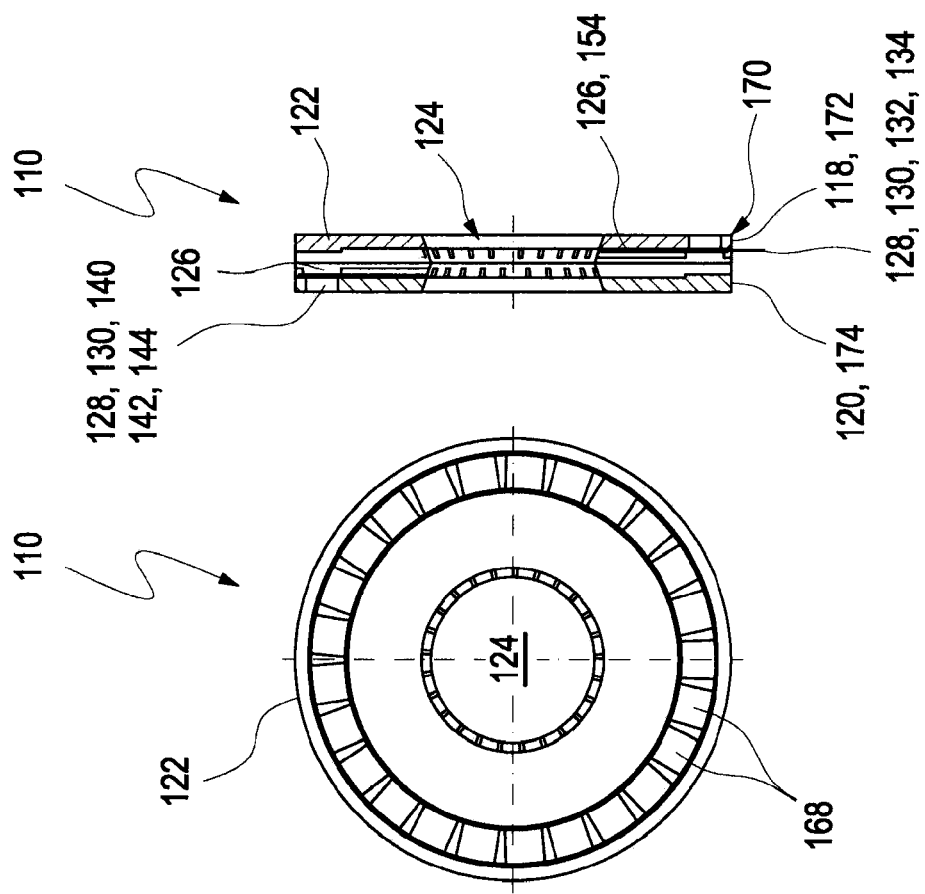
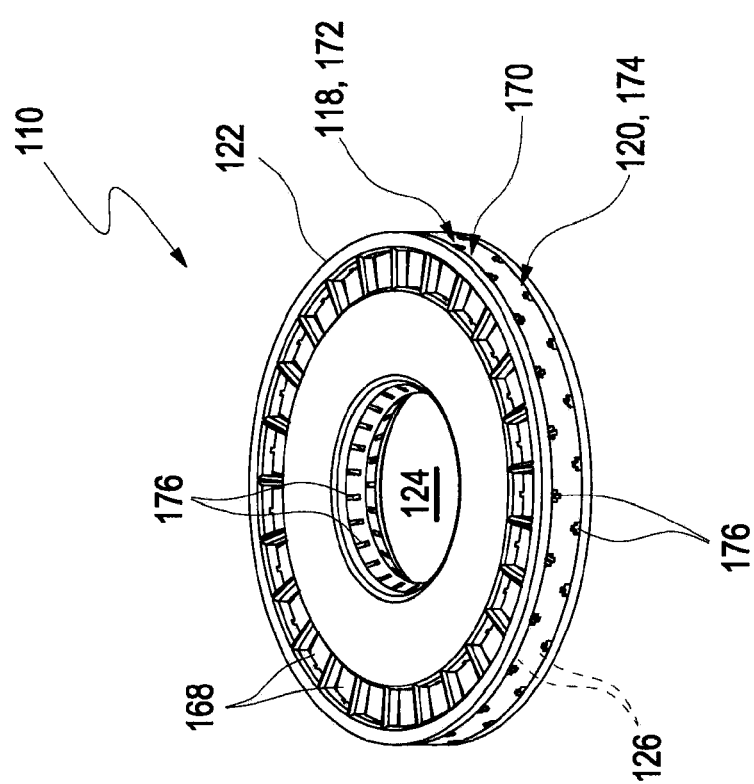
Fig. 2A  Fig. 2B  Fig. 2C

SEQUENCE LISTING

<160> NUMBER OF SEQ ID NOS: 2

<210> SEQ ID NO 1
<211> LENGTH: 261
<212> TYPE: PRT
<213> ORGANISM: Artificial Sequence
<220> FEATURE:
<223> OTHER INFORMATION: Mutant of glucose dehydrogenase from Bacillus
      subtilis comprising mutations E170K and K252L
<220> FEATURE:
<221> NAME/KEY: Variant
<222> LOCATION: (96)..(96)
<223> OTHER INFORMATION: G replaces E of wt sequence
<220> FEATURE:
<221> NAME/KEY: Variant
<222> LOCATION: (170)..(170)
<223> OTHER INFORMATION: K replaces E of wt sequence

<400> SEQUENCE: 1

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Gly
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
            260

<210> SEQ ID NO 2
<211> LENGTH: 261
<212> TYPE: PRT
<213> ORGANISM: Artificial Sequence
<220> FEATURE:
<223> OTHER INFORMATION: Mutant of glucose dehydrogenase from Bacillus -continued

```
    subtilis comprising mutations E170K and K252L
<220> FEATURE:
<221> NAME/KEY: Variant
<222> LOCATION: (170)..(170)
<223> OTHER INFORMATION: K replaces E of wt sequence
<220> FEATURE:
<221> NAME/KEY: Variant
<222> LOCATION: (252)..(252)
<223> OTHER INFORMATION: L replaces K of wt sequence

<400> SEQUENCE: 2

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

SPACE-SAVING MAGAZINING OF ANALYTICAL AIDS

CROSS-REFERENCE TO RELATED APPLICATIONS

This application is a continuation of U.S. patent application Ser. No. 13/212,699, filed Aug. 18, 2011, which is a continuation of International Application No. PCT/EP2010/000865, filed on Feb. 12, 2010, which claims the benefit and priority of European Patent Application Nos. 09153211.9, filed on Feb. 19, 2009 and 09168335.9, filed on Aug. 20, 2009. The entire disclosures of each of the above applications are incorporated herein by reference.

REFERENCE TO A SEQUENCE LISTING

The material in the ASCII text file titled "15878A000053USCOA_SEQLST" is hereby incorporated by reference in its entirety. The ASCII text file titled "15878A000053USCOA_SEQLST" was created on Aug. 19, 2013 and the size is 5,598 bytes.

BACKGROUND

The invention relates to an analytical magazine for receiving a plurality of analytical aids and an analytical system that is arranged for interacting with an analytical magazine according to the invention. Analytical magazines and analytical systems of this kind are used in natural sciences, technology, medicine and/or medical diagnostics, for detecting one or more analytes qualitatively or quantitatively in a sample. For example, these samples can be samples of body fluid, such as urine, blood, interstitial fluid or the like. The analytes to be detected can for example be metabolites. Without limiting further possible fields of application, the invention is described hereunder with reference to the detection of blood glucose. Basically, however, other analytes can also be measured alternatively or additionally, wherein the concept of an analyte can also comprise other measurable properties of the sample, for example coagulates or the like.

Systems are known, in particular from the field of medical diagnostics, but also from other fields, by means of which analytes can be detected in samples. In medical diagnostics said detection, for example of blood glucose, as a rule comprises generating a sample of body fluid, for example blood or interstitial fluid, followed by receiving of said sample and a qualitative and/or quantitative analysis. For this purpose, as a rule one or more analytical aids are used, which for example can comprise a lancet and/or test elements, by means of which the sample can be generated and/or received and/or analyzed.

In particular, integration of various system functions has in the past led, with analytical systems of this kind, for example blood sugar measuring systems, to commercial solutions with interchangeable magazines for the analytical aids, for example magazines of test strips. Typical representatives of this product group are the systems Accu-Chek Compact® and Ascensia Breeze, which are commercially available systems. Typical accompanying magazines as a rule hold 17 or 10 test strips.

In newer systems, in many cases various system functions are integrated, for example the system function of sample generation (for example by perforation of a portion of skin) and the system function of sample reception and optionally also the system function of analysis. When designing more highly integrated systems, blood collection and a testing function for example may be combined. For this purpose, for example so-called "microsamplers" are known, which can combine the function of a lancet and the function of transport of the sample, for example to a test element. A separate pricking aid for taking blood, for example from a finger pad, an ear lobe or some other portion of skin of a test subject, therefore becomes unnecessary.

Several such microsamplers can be accommodated in a changing magazine of a great variety of designs. Basically, regardless of the type of analytical aids, there are three main types of magazines, namely circular magazines (for example in the form of drums and/or disks), linear magazines (for example in the form of stacking magazines, zigzag magazines or similar) and belt magazines, in which the analytical aids are arranged on a belt or some other form of at least partially flexible carrier. These types of magazine can basically also be used, or modified, within the scope of the invention described in the following. In the prior art, circular magazines are described for example in US 2006/0008389, US 2007/0292314, US 2006/0184064, US 2003/0212347 or US 2002/0087056. Linear magazines are described for example in U.S. Pat. No. 6,036,924 or in US 2003/0191415. Belt magazines are for example disclosed in US 2002/0188224, in US 2008/0103415, in EP 1360935 A1 or in DE 19819407 A1.

A driving force for the integration of several system functions is in particular the desire for a safe and simple operation, and miniaturization of the complete system. As frequent changing of the magazine is rather inconvenient and there is the inherent risk of not having a reserve magazine to hand at the decisive moment, a magazine should hold at least 25 test elements, preferably even 50 test elements or more.

However, the systems and magazines known from the prior art pose some technical challenges. Thus, for example the demand for smallest possible system size, at the same time with the maximum possible number of analytical aids per magazine, for example test elements, represents conflicting objectives. Equipment volumes below 130 ml are especially preferred by the user. Commercially, however, up to now it has not been possible to combine this equipment size with a magazine that for example comprises 50 microsamplers.

Circular magazines, for example of the type described above, also have the disadvantage that as a rule the number of analytical aids has a direct influence on the outside diameter of these circular magazines. A high magazine capacity therefore either leads to very flat equipment (for example in the case of disk magazines) or to particularly thick equipment (for example in the case of drum magazines). However, in many cases such equipment does not correspond to the customer's ideas. With linear magazines, on the other hand, the number of available analytical aids as a rule is directly reflected in the length of the magazines. Moreover, in this design, as a rule magazine displacement is necessary after each test, so that twice the space requirement in the system must be reserved for the magazine. The desired system size is most likely to be achieved with belt magazines, as the magazine size depends nonlinearly on the magazine capacity. However, a disadvantage with such systems is in many cases the high mechanical complexity, in particular with respect to belt guidance and/or belt control.

Therefore approaches are known from the prior art, which provide magazines in the form of so-called reversing magazines. Thus, US 2006/0264996 describes a linear magazine for lancets, which is of doubled design, with two such magazines abutting each other end to end. After all the lancets of a first end section of the complete magazine produced in this way have been used up, the magazine is ejected, turned round, and the lancets in a second end section are used.

However, these reversing magazines known from the prior art have the disadvantage that they are designed exclusively for use in pricking aids. The known reversing magazines will not be suitable for an integration concept, i.e. use in systems in which several system functions are integrated. However, these integrated systems, in particular systems with so-called microsampler magazines, have a number of special requirements. Thus, as a rule the analyte must be detectable in the magazine, for example optically and/or electrochemically. Furthermore, integrated test elements, for example test chemistries, should have a guarantee with respect to their stability, so that a reliable expiry term can be stated. Furthermore, cross-contamination of the analytical aids, in particular of the microsamplers, should be prevented. To date, these requirements are on the whole not fulfilled, or only fulfilled inadequately, with known analytical systems and known analytical magazines.

SUMMARY

Therefore a problem to be solved by the present invention is to provide an analytical magazine and an analytical system, which at least largely avoid the disadvantages of known magazines and/or systems. In particular, the analytical magazine should be designed for use in microsampler systems.

This problem is solved by an analytical magazine and by an analytical system with the features of the independent claims. Advantageous further embodiments of the invention, which can be realized individually or in combination, are presented in the dependent claims.

An analytical magazine is proposed, which comprises a plurality of analytical aids accommodated in chambers, preferably at least 10 analytical aids, in particular at least 20, at least 30, at least 40 and especially preferably at least 50 analytical aids or more. The analytical magazine serves for use in an analytical system. An analytical system is to be understood generally as a system that performs at least one analytical function. An analytical function is to be understood as the detection of at least one analyte in a sample. Without limitation, it is assumed in the following that the sample is a sample of a body fluid. Basically, however, it would also be possible to analyze other samples. The concept of at least one analyte is basically to be interpreted widely and comprises, in addition to substances to be detected, for example of one or more metabolites, basically also other measurable properties of the sample. Especially preferably, however, the invention is used for detecting at least one metabolite in a body fluid, for example for detecting blood glucose, cholesterol, (anti-) coagulants or the like.

Correspondingly, an analytical magazine is to be understood as a magazine that is designed for use in such an analytical system. For example, for this purpose the magazine can comprise one or more housings, which can be inserted in one or more housings of the analytical system. For this purpose, for example corresponding orientation aids, connecting elements, rails, hooks, grooves, projections, transport elements or combinations of the aforesaid and/or other elements can be provided on the analytical magazine, which make possible or at least simplify interaction of the analytical magazine with the analytical system. For example, transport elements and/or positioning aids can be provided, which enable positioning or correct orientation of the magazine within the analytical system.

An analytical aid is accordingly to be understood generally as an aid that is arranged so as to enable the analytical system to detect the at least one analyte in a body fluid and/or to interact at least partially with components of the analytical system in the detection of the at least one analyte in the body fluid. In particular, the analytical aids can be disposables, i.e. aids that are designed to be used once. The analytical magazine comprises a plurality of chambers, thus at least two chambers, in which in each case at least one of the analytical aids is or can be accommodated. For example, exactly one analytical aid can be accommodated in each case in each chamber. This can be the case for example with disk-shaped or bar-shaped analytical magazines. Alternatively, also several analytical aids are or can be accommodated in one chamber. This can for example be achieved in the case of belt magazines, in which for example a "good reel" with a plurality of still unused analytical aids is accommodated in a first chamber and a "bad reel", on which a plurality of used analytical aids can be received, is accommodated in a second chamber. The analytical aids can optionally in their turn be composed of partial aids, which can be of continuous design, or which optionally can also be formed independently of one another, for example can be actuated or used independently of one another. The totality of all partial aids in a chamber, which colloquially is often called a "test", can then generally be regarded as an analytical aid in the sense of the above definition.

In particular, the analytical aids can comprise one or more of the types of analytical aids described hereunder, optionally also as partial aids. Thus, the analytical aids can comprise for example at least one test element, for example in each case at least one test element, wherein the at least one test element has at least one test chemistry, which is designed to change at least one property if an analyte to be detected is present. This test chemistry can for example be in the form of one or more test fields. Moreover, the test chemistry can for example be integrated at least partially in a housing of the analytical magazine, in particular in a wall of the chambers. For example, the test chemistry can be designed so that in each case at least one test field is assigned to one internal space of one chamber. The test chemistry can also be designed for several or all chambers simultaneously, for example in the form of a common test field for several or all chambers of the analytical magazine. For example, a test chemistry disk can be provided, for example in the form of a test chemistry ring, wherein in each case at least one part of the surface of said test chemistry disk, for example of the test chemistry ring, is assigned to the internal spaces of the chambers, so that these regions in each case form their own separate test fields in the individual chambers.

The at least one property, from the change of which it is possible to draw a conclusion about the presence and/or absence of the at least one analyte qualitatively and/or quantitatively, can for example comprise at least one chemically and/or physically measurable property. For example, it can be an electrochemically and/or optically measurable property, for example a color change or the like. Examples of said test chemistries, which basically can also be used within the scope of the present invention, are in particular described in J. Hönes et al., Diabetes Technology & Therapeutics, Volume 10, Supplement 1, 2008, pages S-10 to S-26. Furthermore, reference may be made for example to WO 2007/012494 A1 (see also, US 2008/0213809), in which particularly moisture-stable test chemistries are described. The test chemistries stated in these publications can also be used, individually or in combination, within the scope of the present invention. In particular, highly specific test chemistries can be used, with which the detection reacts specifically to the at least one analyte. Other types of test chemistries can basically also be used.

Alternatively or additionally to test elements, the analytical aids can also comprise one or more lancets for producing at least one opening in a test subject's skin. A lancet is generally to be understood as a device which, for example by a prick and/or an incision, produces such an opening, through which the body fluid can be taken from a tissue of the test subject. For example, for this purpose the lancets can comprise at least one point and/or at least one blade. In particular, these lancets can be round lancets and/or flat lancets, i.e. lancets which are machined, for example etched, from a flat component, for example sheet metal.

Alternatively or additionally to the aforesaid aids, the at least one analytical aid can comprise at least one transfer element for receiving a sample of a body fluid and/or for transferring the sample, in particular for transferring the sample to at least one test element, for example of the type described above. A transfer element can be understood for example as an element which takes up the sample and then, by executing a movement, transfers it to the test element. Alternatively or additionally, however, other transfer mechanisms can also be used, for example transfer mechanisms that are based on capillary forces. Thus, again alternatively or additionally, the analytical aids can also comprise one or more capillary elements for receiving and/or transferring a sample of a body fluid, in particular to the at least one test element. A capillary element is generally to be understood as an element which, by utilizing a capillary force, performs a transport operation and/or a collecting operation.

The stated possibilities can also be combined individually or in groups. Thus, the analytical aids can for example also comprise one or more microsamplers. Said microsamplers can comprise a spatially narrow intermeshing of a suction needle and a test element. For example, the blood to be analyzed can be transferred, without the user's assistance, from a wound or opening to a test element. For example, for this it is again possible to use a lancet, for example a needle with a capillary suction channel. In general, the microsamplers should comprise at least one lancet for making at least one opening in a test subject's skin and at least one capillary element for receiving and/or transferring a sample of a body fluid, wherein the transfer can once again preferably be effected at least partially to at least one test element. However, the transfer can additionally be supported by a spatial movement of the microsampler, for example by means of at least one actuator.

The invention is described in the following with reference to the preferred embodiment in which the analytical aids are at least partially arranged so that, in a sampling movement, a sample of a body fluid is received and is transferred completely or partially to a test element. A sampling movement generally means a movement of the analytical aid and/or of a partial aid, which first takes place from the analytical system toward the surface of the test subject's skin, followed by a return movement to the system. In the forward movement, for example perforation of the skin can be performed, for example by means of one or more of the aforementioned lancets. Already during perforation and/or following perforation, sampling can take place, for example collection of a sample, for example simply by applying the sample on a transfer element and/or suction of the sample into the transfer element, for example a capillary element. Then a return movement of the analytical aid can take place, which can also still be a component part of the sampling movement. In the sampling movement, in particular in or after the return movement, the sample can be transferred to a test element, which can be a component part of the analytical aid, which participates in the sampling movement and/or which can also be received as an at least partially immobile partial aid in the chambers. Examples are described below in more detail. The transfer of the sample to the at least one test element can take place for example at, during or after a remagazining of the analytical aid, which is described in more detail below, i.e. an operation in which the analytical aid is received again completely or partially in a chamber, in particular the chamber from which it was taken previously.

For accommodation of the analytical aids in the chambers, basically at least two principles of accommodation in the chambers are conceivable. For example, one analytical aid can be accommodated per chamber, in particular an analytical aid that comprises at least one partial aid in the form of a test element with a test chemistry. Optionally, preferably additionally, at least one further partial aid in the form of a lancet and/or a microsampler can be provided per chamber. In this principle, the analytical aids can in particular be remagazined in the same chamber after use. Alternatively, however, remagazining in another chamber is also possible. This first principle is preferred in particular in the case of disk-shaped or bar-shaped magazines. According to another principle, at least one first chamber can be provided for unused analytical aids and at least one second chamber for used analytical aids. In this case, for example for use, the analytical aids can be taken from the first chamber and, after use, can be transferred to the second chamber, which can be formed spatially separately from the first chamber. This principle can be used for example for belt magazines, wherein for example a "good reel" for receiving unused analytical aids is provided in a first chamber and a "bad reel" for receiving used analytical aids is provided in a second chamber.

According to the invention, in a first aspect of the present invention it is proposed in particular to set up the analytical magazine in such a way that it can be accommodated in at least two orientations in the analytical system. In particular the analytical magazine can be arranged in such a way that it can, in the at least two orientations, be connected to the same interface of the analytical system, for example an interface with at least one transport function and/or at least one actuator function, for example for executing the sampling movement, and/or at least one measuring function, for example an optical and/or electrochemical measuring function.

For this purpose the analytical magazine can for example be designed at least partially with a symmetry, in particular a symmetry about at least one axis of symmetry. The analytical magazine can accordingly be designed for example as a reversing magazine, which can be inserted in the at least two orientations in the analytical system and can preferably connect there to the same interface in all orientations.

An orientation is generally to be understood preferably as an angular orientation of the analytical magazine, for example relative to a coordinate system of the analytical system, thus an orientation with respect to one or more angular coordinates, for example spatial angular coordinates. Alternatively or additionally, however, an orientation can also be understood as an absolute orientation, for example using one or more Cartesian coordinates. However, the embodiment of the magazine as a reversing magazine is especially preferred, for example in such a way that in a first orientation the analytical magazine can be removed from the analytical system, so that it can then be rotated through one or more angles, and then accommodated again in the analytical system in at least one second orientation, different from the first orientation. In particular, the rotation can be a rotation through 180° about an axis, optionally followed by at least one further rotation, for example an angular-offset rotation about an axis rotated through 90° to the first axis, for example through an offset angle described below in more detail. The magazine can for example be designed completely as a reversing magazine, so that the two orientations differ from one another by 180° with respect to an axis of rotation.

In particular, the analytical magazine can be designed in such a way that, apart from the desired at least two orientations that are different from one another, it does not allow any other orientations. For example, as described above, one or more elements can be provided, which make it possible for the analytical magazine to be inserted in the analytical system in exactly the orientations envisaged, but not in other orientations. For example, a housing of the analytical magazine can be designed in such a way that it makes insertion in the analytical system only possible in the orientations envisaged, but not in other orientations. For this purpose the housing can for example have a corresponding shape, for example a symmetrical shape in the sense of the above definition, for example a symmetry with respect to one or more axes of rotation. The housing can also for example have corresponding elements, for example grooves, rails, projections, ridges or similar elements, which prevent the analytical magazine being inserted in the analytical system in an orientation that is not envisaged.

The analytical magazine is thus arranged so that, in the various orientations, in each case the analytical system is provided with a plurality of analytical aids, for example so that in each orientation the analytical system can be provided with a plurality of chambers with in each case at least one analytical aid. These analytical aids can for example be provided successively, for example via a corresponding transport mechanism of the analytical system, which brings the respective chambers available in that orientation successively into an application position. In this way, the analytical magazine differs for example from simple drum magazines, which after the drum indexes to the next chamber are admittedly also arranged in a different orientation, but in an orientation in which only one analytical aid is provided.

An orientation is therefore to be understood as an orientation of the analytical magazine as a whole, in which the analytical system can be provided with analytical aids from the partial magazine belonging to this orientation. An orientation is then in each case preferably assigned to precisely one partial magazine. Each orientation can be divided into several sub-orientations, for example angular positions of a magazine disk, which can be occupied successively on further indexing. However, these sub-orientations are, as before, assigned to an orientation of the analytical magazine, for example an orientation in which a partial magazine is located at an application level and/or an application position of the analytical system. It is only after the orientation has been changed, for example by turning the analytical magazine by rotation through 180°, that another partial magazine reaches the application level or application position and can supply its analytical aids to the analytical system.

By means of the analytical aids, at least one sampling movement according to the above definition can be executed. In particular the analytical system can comprise one or more application positions, wherein the analytical system can be arranged to use in each case the at least one chamber actually located in the application position, or the at least one analytical aid in this chamber, for the sampling movement. For example, the analytical system can comprise one or more actuators, by means of which the sampling movement can be executed. For the sampling movement, the whole analytical aid can be moved and/or also optionally only at least one partial aid. If the analytical aids comprise for example at least one lancet and/or at least one microsampler and/or at least one transfer element, then these lancets or microsamplers or transfer elements can be used for the sampling movement, whereas other partial aids of the analytical aids can remain in the chamber, for example one or more test elements. However, other embodiments are also possible, for example embodiments in which test elements take part completely or partially in the sampling movement. However, an embodiment is described below, in which the test elements remain within the chambers, whereas microsamplers perform the sampling movement and transfer a sample of the body fluid to the test elements in the chambers.

In the first aspect of the present invention, the analytical magazine is arranged to permit remagazining of the analytical aids. Remagazining is to be understood as an operation in which the analytical aids, preferably during or after complete execution of the sampling movement, are transferred, completely or partially, back again into the same chamber from which they had been taken, or, alternatively or additionally, into a separate chamber. Generally the analytical magazine according to the invention is thus designed in such a way that said return is technically possible and is not prevented for example by barbs or similar configurations.

For the purpose of remagazining, the analytical aids can for example also be arranged to interact with the analytical system in such a way that said remagazining becomes possible. Thus, the analytical aids can for example have at least one coupling element, by means of which remagazining of the analytical aids becomes possible, in particular remagazining in the chambers from which the respective analytical aids had been taken. For example these coupling elements can have one or more grooves, hooks, projections, recesses, loops, pilot holes or other coupling elements or combinations thereof and/or other coupling elements. Said coupling elements can for example be taken from the prior art. Thus, reference may be made for example to the coupling elements described in US 2006/0008389 A1, with which an actuator is connected by means of one or more hooks to the analytical aids and then disconnected from these again, for example for a sampling movement and a subsequent remagazining. Coupling elements of this kind can also be used within the scope of the present invention. However, other types of couplings can basically also be used, for example a frictionally engaged or positive-fit coupling of an actuator to the analytical aid and/or partial aid, for example by means of a gripper or a similar device.

The coupling elements can in particular have one or more actuators coupled to them, for example coupling rods, which can be a component part of the analytical system, and which bring about both an advance of the analytical aids and a return of the analytical aids within a sampling movement, with subsequent remagazining. For example, corresponding coupling rods, tappets or similar can be provided.

In the first aspect of the present invention the analytical magazine is arranged to hold the analytical aids and/or partial aids in the chambers after remagazining. Holding is to be understood as an operation in which falling out or sliding out of the analytical aids from the chambers, for example through openings in a seal of the chambers created during the sampling movement, is at least largely prevented. For this purpose, one or more holding elements can be provided for example in the analytical magazine and/or on the analytical aid or partial aid, for example in each case at least one holding element per chamber, which effect such holding after remagazining. For example, these holding elements can comprise hooks, narrowings, projections, loops, stops or similar elements or combinations thereof and/or other elements. Moreover, in each case partial holding elements can be provided on the analytical aids or partial aids, which interact with corresponding partial holding elements of the chambers.

Alternatively or additionally to the use of one or more holding elements, the holding of the analytical aids after remagazining can also be achieved in some other way. For example, the analytical aids can also be held in place at least partially positively and/or nonpositively. This form closure and/or force closure can for example also only take place during remagazining and/or after remagazining. For example, during remagazining, the analytical aid and/or partial aid can be brought into a remagazining position in the magazine, for example in the chamber, in which this force closure and/or form closure first occurs. This remagazining position can be identical to or different from a position in which the analytical aids and/or partial aids are before the sampling movement. The form closure and/or force closure can for example also be connected with deformation of the analytical aids and/or partial aids. For example, the chamber can be of a design such that the analytical aid and/or partial aid, for example a lancet and/or a microsampler, is curved in the chamber and preferably is pressed by a restoring force against a chamber wall. In this way a force closure, in particular a frictional closure, can be achieved. For example, the chamber can be of curved shape, so that the analytical aid and/or partial aid is bent in the chamber. The lancet or the microsampler can for example be made completely or partially of an elastic material, for example a metallic material, for example sheet metal, which can provide the aforementioned restoring force. Alternatively or additionally, the chamber can also for example be constructed with an elastic wall, which is deformed by the analytical aid and/or partial aid during remagazining, wherein restoring forces of the chamber wall can bring about the aforesaid force closure, in particular the frictional closure. Also in this way, by adapting the chamber geometry and/or the geometry of the analytical aid and/or suitable selection of materials of the analytical aid and/or of the housing, a corresponding holding of the remagazined analytical aid can be effected. Combinations of the aforesaid possibilities and/or other possibilities for holding are also conceivable.

In the first aspect of the present invention, the analytical magazine comprises at least two essentially identical partial magazines, wherein each partial magazine comprises a plurality of analytical aids, for example a plurality of similar analytical aids, which for example can each be accommodated in individual chambers. Essentially identical partial magazines are to be understood as magazines that are of identical design, so that these partial magazines can replace one another in the aforementioned possible different orientations of the analytical magazine. Each partial magazine can for example provide a particular orientation of the analytical magazine, which can also be called the application orientation, and in which the respective partial magazine can interact with the analytical system. For example, the analytical system can have an application position, wherein in the application orientation in each case one of the partial magazines is arranged in the application position and/or application level of the analytical system and/or can provide the analytical system with analytical aids or partial aids. The partial magazines do not necessarily have, but preferably have, in each case the same number of analytical aids.

For example, two partial magazines can be provided, stacked one above the other. The partial magazines can, for example after rotation through 180° and optionally at least one further rotation about another axis, for example an offset-angle rotation, make it possible for the magazine to be reinserted in the analytical system. The partial magazines can for example be arranged on different levels, for example in the form of partial magazines stacked one above the other. This stacking should take place in such a way that after changing from one possible orientation to another possible orientation, the partial magazine belonging in each case to this orientation can interact with the analytical system, for example with one and the same interface of the analytical system, preferably suitable for all orientations. The analytical magazine thus differs for example from magazines in which simple test elements are arranged side by side.

The analytical magazine can advantageously have further design features. Thus, the analytical magazine, as already described above, can be provided at least partially with a symmetry, in particular a symmetry about at least one axis of symmetry.

The analytical magazine can in particular have at least one indicating element, preferably a plurality of indicating elements, the number of which can correspond for example to the number of possible orientations. The indicating element can be designed to be detected by the analytical system and to provide the analytical system with at least one piece of information about a current orientation. The indicating element can for example comprise at least one simple, nonvariable element, which can be detected by the analytical system. Alternatively or additionally, however, the indicating element can also comprise one or more variable elements, which for example can be altered by the analytical system, for example film elements, which can be pierced after a chamber is used, magnetic storage elements writable by the analytical system, or the like.

The analytical aids can be arranged in the analytical magazine in at least two levels of aids, wherein after a change of orientation in the analytical system, in each case a new level of aids is arranged at least partially in an application level of the analytical system. An application level means a level of the analytical system which has at least one application position, i.e. a position in which an analytical aid can be used by the analytical system, for example for a lancet movement, a sampling movement, a measurement of an analyte concentration or similar purposes. A level of aids means a common level of a collection of analytical aids that are usable in the same orientation, which for example can in fact be arranged in the same level or can easily be moved to this level.

The analytical magazine can basically have one or more of the basic forms already described above and/or also other forms, for example a circular magazine form (for example in the form of a drum and/or a disk), a linear magazine (for example a stacking magazine and/or a zigzag magazine) and/or a belt magazine. In this respect, reference may be made for example to the prior art, wherein the systems described there can be modified according to the invention into reversing magazines or into analytical magazines that can be received in at least two orientations in the analytical system. It is especially preferable if the analytical magazine is constructed in the form of a circular magazine, in particular in the form of a round disk, wherein the analytical aids are preferably aligned in the analytical magazine at least approximately in a radial arrangement. In these disk magazines, which can for example comprise the analytical aids in at least two levels of aids, the advantages of the reversing magazines are particularly pronounced, because the magazine capacity can be increased without having to increase a diameter of the round disk. Because as a rule the thickness of the disk is much smaller compared to its diameter, increases in thickness, for example because of providing several levels of aids, are less noticeable, from design aspects, than an increase in a radius of the disk. However, analytical magazines other than disk-shaped magazines can basically also be constructed according to the invention, for example stick magazines and/or strip magazines.

If the analytical magazine is constructed completely or partially as a circular magazine, in particular as a circular magazine in the form of a round disk, it is especially preferable to arrange the analytical aids in different levels of aids with an angular offset to one another. For example, in a first level of aids the analytical aids can be aligned equidistantly and radially, and so too in a second level of aids different from the first level of aids. In this case it is especially preferable if the stated offset-angle is provided, so that for example between two adjacent aids of a first level of aids in a projection onto the second level of aids, an analytical aid is arranged with an offset-angle exactly between the two analytical aids of the first level of aids. In this way it is possible for example to ensure that all aids of all levels of aids are accessible from two directions perpendicular to the levels of aids, which are preferably arranged parallel to one another, without said access being blocked by analytical aids in other levels of aids.

Generally it is thus especially preferable to arrange the different levels of aids parallel to one another. Furthermore it is generally preferable, also with other embodiments than that described, if the analytical magazine is arranged in such a way that, in all possible orientations of the analytical magazine in the analytical system, access is provided to a chamber located in an application position of the analytical system and/or at least one analytical aid is accommodated in said chamber, from at least two directions, in particular from directions opposite to one another, in particular from directions perpendicular to the levels of aids.

In particular, by means of one or more of the embodiments described above, but also in other ways, according to the invention analytical magazines can be produced with a high packing density. In particular, said high packing density can be produced with the aforementioned circular magazines, in particular the aforementioned disk-shaped magazines, in particular with radial orientation. In contrast to the prior art, in which such increases in packing density are as a rule associated with an increase in radius, this can take place while the radius remains the same. In particular, in this way analytical magazines can be produced that have one or more of the following properties: A total volume of not more than $10 \text{ cm}^3$, preferably of not more than $8 \text{ cm}^3$ and especially preferably of not more than $7.5 \text{ cm}^3$; an outer radius of not more than 5 cm, preferably of not more than 3 cm and especially preferably of not more than 2.5 cm; an inner radius between 0.5 cm and 2 cm, in particular between 1.0 cm and 1.5 cm and especially preferably of about 1.2 cm; a thickness of not more than 1 cm, especially preferably of not more than 0.5 cm; a number of analytical aids between 10 and 100, in particular between 20 and 70 and especially preferably of 50; a volume between $3 \text{ cm}^3$ and $30 \text{ cm}^3$, in particular between $5 \text{ cm}^3$ and $10 \text{ cm}^3$ and especially preferably of $7.5 \text{ cm}^3$; a packing density of the analytical aids of more than $5/\text{cm}^3$, in particular between $5/\text{cm}^3$ and $10/\text{cm}^3$, for example between $6/\text{cm}^3$ and $7/\text{cm}^3$ and especially preferably of $6.7/\text{cm}^3$. For example, the analytical magazine can be constructed as a circular disk-shaped magazine, with an outer radius of approx. 2.5 cm, an inner radius of approx. 1.2 cm, a thickness of approx. 0.5 cm, a number of analytical aids of 50 and therefore a volume of $7.5 \text{ cm}^3$ and a packing density of $6.7/\text{cm}^3$.

A packing density means a ratio of the number of analytical aids and/or a number of chambers to the construction volume of the analytical magazine. For example, for a reversing disk according to the invention with 50 mm diameter the packing density can be 50 analytical aids/$5.97 \text{ cm}^3$ (i.e. for example 50 chambers), compared with a simple disk with 50 mm diameter and approx. 3 mm thickness, which for example can have a packing density of 50 analytical aids/$5.42 \text{ cm}^3$. The analytical aids are often also called "tests", regardless of their function and design. A "test" can thus generally mean at least one analytical aid, which can be used for a testing operation. It can for example be a test element or a lancet or even a pair comprising a test element and a lancet, which belong together and can be used for joint sampling and subsequent analysis, preferably with exactly one test stored in exactly one chamber. An analytical aid or a test can thus for example comprise several related partial aids. It is especially preferable if each analytical aid comprises at least one analytical partial aid in the form of a test element with a test chemistry. Alternatively or preferably, in addition each analytical aid can further comprise an analytical partial aid in the form of a lancet and/or a microsampler. In each case one analytical aid or one test can for example be accommodated in precisely one chamber. However, within the scope of the present invention, here and in the following, no further distinction will be made between a test and an analytical aid linguistically and as regards content, including the possibility that a test or an analytical aid can comprise several partial aids, for example in each case a test element and a lancet. The reversing disk can for example have a thickness of 5 mm and a diameter of 42 mm. In the stated cases, in each case the central holes in the magazine are also taken into account, as this space can also be used for device mechanisms.

As shown above, the analytical aids can in particular be constructed at least partially as so-called microsamplers, i.e. as analytical aids which should make possible both production and collection of the sample and optionally also an analysis of the sample. For this purpose the microsamplers can for example comprise at least one lancet and at least one capillary element. In general, the analytical aids can be arranged at least partially to collect, during the sampling movement, a sample of a body fluid and transfer it to a test element, wherein the transfer of the sample can in particular take place at least partially during the remagazining of the analytical aid.

The analytical aids can, as described above, in particular have a test chemistry, which can be arranged to alter at least one property when an analyte to be detected is present. For example, reference may be made to the types of known test chemistries described above, which can also be used within the scope of the present invention. In particular this test chemistry can be contained in the form of at least one test field. In particular said test fields can be accommodated at least partially in the chambers. For example, the test fields can be inserted completely or partially in the chambers and/or also can be integrated in the chambers, for example in the chamber walls. For example, in the chamber walls and/or on and/or in openings provided in the chamber walls, test fields can be accommodated, whose surfaces in each case face the interior of the chambers or are accessible from the interior of the chambers. The analytical system can support the transfer of the sample onto these test fields, for example in that one or more actuators are provided, which press microsamplers and/or lancets and/or transfer elements, after they have collected the sample, onto the at least one test field and/or bring them into the vicinity of this at least one test field, so that the sample is transferred to this at least one test field. Various examples of implementation are described below in more detail.

The analytical magazine can in particular be designed in such a way that, in each of the possible orientations, it provides a plurality of analytical aids, for example a plurality of similar analytical aids, for example an equal number of analytical aids in each orientation. As described above, the analytical magazine is preferably designed in such a way that the different partial magazines can interact, in their respective application orientation, with the same interface of the analytical system, so that it is not necessary to provide different interfaces in the analytical system for the different partial magazines. The interface can for example comprise a mechanical interface, for example for further indexing of the individual chambers of each partial magazine (for example by a rotation and/or a linear displacement) and/or for a mechanical coupling to the analytical magazine and/or the analytical aids, for example for the purpose of executing a sampling movement, and/or a measuring interface, for example an optical and/or an electrical measuring interface. The analytical system, in particular the interface, can have at least one measuring system, which can be arranged to interact with the test elements for detecting the at least one analyte. The analytical magazine can be arranged in such a way that the test elements, after a change of orientation, interact with the same measuring system, without this having to be adjusted substantially to the reoriented magazine. For example a particular application position and/or application level of the analytical system can be provided, wherein the measuring system can interact with the analytical aids (for example a test element and/or test field) of the chamber of the partial magazine that is directly in the application position. Thus, for example one and the same detector can be used for all test elements and/or test fields of all chambers of all partial magazines.

The measuring system can be adapted to the design of the analytical magazine and/or of the test elements. If these test elements are optical test elements, i.e. test elements which, on interaction with the at least one analyte, change at least one optically detectable property, then it can for example be an optical measuring system. Such an optical measuring system can for example comprise at least one optical detector, by means of which the optical property can be detected. Additional elements can also be comprised, for example one or more illuminating devices and/or one or more optical systems. Alternatively or additionally, other types of detection can be used, for example electrochemical detection. For this purpose, for example corresponding electrical and/or electronic measuring devices can be provided, for example for performing amperometric measurements on the test elements.

The measuring system can for example be arranged to interact in at least one application position with the at least one test element, which is located in the at least one application position and/or with the respective chamber in the application position. This application position, in which the measurement takes place, can be completely or partially identical to the application position in which the sampling movement can take place. However, other embodiments are basically also possible, for example sampling movements and measurements in different application positions.

In the embodiment according to the invention that is described, the measuring system can in particular be designed to perform the measurements by means of the same measuring system, even after the orientation has been changed. In this way it is possible to save space in the analytical system and the analytical system can be greatly simplified. To make this possible, the analytical magazine can for example be designed in such a way that the different orientations, for example the analytical aids in the different levels of aids, even after changing the orientation, are again stored essentially right next to one another, so that for example once again one chamber and/or one analytical aid is arranged in the at least one application position.

It has already been described that the analytical magazine preferably has a plurality of properties with respect to its dimensioning, in particular with respect to its packing density. The aforementioned dimensions or even smaller dimensions, which are connected directly or indirectly with the packing density, can basically be achieved even without the embodiment described above of the analytical magazine as reversing magazine with at least two possible orientations. Accordingly, in a second, subordinate aspect of the present invention, generally an analytical magazine is proposed, which in particular, but not necessarily, can be formed according to one or more of the embodiments described above. Other embodiments are, however, also possible, in particular embodiments in which the analytical magazine is not constructed as a reversing magazine or as a magazine with two possible orientations. In particular, the additional features of the preferred embodiments of the first aspect described above can also be realized in the second aspect of the invention, independently of the first aspect.

The analytical magazine according to the second aspect of the invention has at least two chambers, in which analytical aids can be accommodated. The analytical aids are accommodated in at least one of the chambers. The analytical aids comprise in each case at least one test element with at least one test chemistry for detecting at least one analyte in a liquid sample, in particular a body fluid.

In conventional analytical magazines and test elements, in particular for detecting glucose, as a rule a test chemistry is used that is sensitive to humidity and which, if exposed to air for too long, can suffer impairment or even complete loss of its function. Accordingly, for example conventional test strips must be stored in containers that are impervious to the humidity of the air. These containers are usually partially filled with a drying agent, i.e. a moisture-absorbing material, for example activated charcoal. Now if, in integrated systems, analytical magazines and/or analytical aids, for example disposables, are developed, in which test elements are packed individually or in groups, this packaging must also be of moisture-proof design. However, this requirement for moisture-proof properties greatly limits the selection of potential materials, in particular potential materials for the housing. This is in particular because as a rule there are additional requirements, which must be fulfilled simultaneously. Thus, the materials used must in most cases be sterilizable, in particular by means of ionizing radiation. Alternatively or additionally the materials used must as a rule not emit gases, in particular not after or during irradiation in a sterilization process. Once again, alternatively or additionally, the materials used must be suitable for the chosen production process, for example for injection molding and/or some other forming process. Once again, alternatively or additionally, the materials used should preferably be biocompatible and/or should be joinable and/or sealable. There may be further requirements. In particular the requirements for moisture-proof properties are difficult to fulfill in practice, as most plastics are open to diffusion of moisture, in particular at small wall thicknesses, for example wall thicknesses of less than a millimeter.

According to the invention, it is therefore proposed in the second aspect of the present invention, as well as in the third aspect of the invention described in more detail below, to design the test chemistry in such a way that it is at least largely stable to environmental effects, in particular to moisture. The test chemistry can in particular be in the form of dry chemistry, in particular on a test strip. Within the scope of the present invention, a test chemistry essentially stable to environmental effects means a test chemistry that is stable to humidity and advantageously also to sterilization processes, in particular sterilization processes using ionizing radiation. Stable means if, in storage at 32° C., a relative air humidity of 85% at normal pressure for a period of three weeks, the activity, for example the enzyme activity of the test chemistry of the analytical aid, decreases by less than 50%, preferably by less than 30% and especially preferably by less than 20%. The activity can basically be determined by any method known from the prior art, because within the scope of the definition given, only a ratio of the decrease in activity measured with this method to an activity measured with this method before storage or immediately after production of the analytical aid is of relevance. The activity can refer in particular to an enzyme activity of a dry chemistry, in particular in a test strip. For example, methods are known which, for measuring enzyme activity, extract the enzyme from the test chemistry or the test strip and then determine the activity for example by means of ultraviolet absorption. In this connection, reference may be made for example to H. U. Bergmeyer: Methoden der enzymatischen Analyse [Methods of enzymatic analysis], Verlag Chemie, 2nd edition 1970, p. 417 or to Banauch et al.: A glucose dehydrogenase for the determination of glucose concentrations in body fluids, Z. Klin. Chem. Klin. Biochem. 1975 March; 13(3):101-7. For example, for the test, a test strip can be prepared with the test chemistry, the enzyme activity of an enzyme of the test chemistry can be measured with a usual method, then the storage described above is carried out and then the same method is used again for measuring the enzyme activity. This procedure is usually carried out with a representative set of test strips or test chemistries. Alternatively or additionally, stability to environmental effects in the form of air humidity can preferably also be supplemented with high stability of the test chemistry to environmental effects in the form of radiation usually employed for sterilizing the analytical aids and/or the analytical magazines as a whole, for example gamma radiation and/ or beta radiation and/or some other kind of ionizing radiation.

As an example of said test chemistry, stable to environmental effects, reference may be made to WO 2007/012494 A1, cited above. The test chemistry presented there can also be used within the scope of the present invention, alone or also in combination with one or more other test chemistries. Alternatively or additionally, the test chemistry can also be designed as described in EP 2093284 A1 or WO 2009/103540 (see also, US 2011/0143416).

Thus, the test chemistry can for example contain an enzyme and a stable coenzyme, which are stored together. It was found, surprisingly, that with the aid of a stable coenzyme, long-term stabilization of several weeks or months is possible at high relative humidity or even in the liquid phase and at elevated temperatures. This finding is surprising, as it is known that, in the presence of native coenzyme, enzymes do indeed possess an increased short time stability for some hours, but display a lower stability over a longer period. Against these findings relative to the prior art, it was surprising that an enzyme in the presence of a stable coenzyme has a far greater long-term stability than an enzyme in the presence of a native coenzyme, in particular as the stable coenzymes possess a lower binding constant with the enzyme than the native coenzyme.

The enzyme stabilized by the method according to the invention can in particular be a coenzyme-dependent enzyme. Suitable enzymes are e.g. dehydrogenases, selected from a glucose dehydrogenase (E.C.I.1.1.47), lactate dehydrogenase (E.C.I.1.1.27, 1.1.1.28), malate dehydrogenase (E.C.I.1.1.37), glycerol dehydrogenase (E.C.I.1.1.6), alcohol dehydrogenase (E.C.I.1.1.1), alpha-hydroxybutyrate dehydrogenase, sorbitol dehydrogenase or amino acid dehydrogenase, e.g. L-amino acid dehydrogenase (E.C.I.4.1.5). Other suitable enzymes are oxidases, such as glucose oxidase (E.C.I.1.3.4) or cholesterol oxidase (E.C.I.1.3.6) or aminotransferases, e.g. aspartate or alanine aminotransferase, 5'-nucleotidase or creatine kinase. The enzyme is preferably glucose dehydrogenase.

The use of a mutated glucose dehydrogenase has proved especially preferable. The term "mutant", as used in the context of the present application, denotes a genetically modified variant of a native enzyme, which at equal number of amino acids, possesses an altered amino acid sequence relative to the wild-type enzyme, i.e. differs in at least one amino acid from the wild-type enzyme. Introduction of the mutation(s) can be site-specific or non-site-specific, preferably site-specific using recombinant methods known by a person skilled in the art, wherein, depending on the particular requirements and conditions, at least one amino acid exchange results within the amino acid sequence of the native enzyme. Especially preferably, the mutant has increased thermal or hydrolytic stability relative to the wild-type enzyme.

The mutated glucose dehydrogenase can contain the altered amino acid(s), relative to the corresponding wild-type glucose dehydrogenase, basically in any position of their amino acid sequence. Preferably the mutated glucose dehydrogenase comprises a mutation in at least one of the positions 96, 170 and 252 of the amino acid sequence of the wild-type glucose dehydrogenase, wherein mutants with mutations in position 96 and position 170 or mutations in position 170 and position 252 are especially preferred. It has proved advantageous if the mutated glucose dehydrogenase does not contain other mutations apart from these mutations.

The mutation in positions 96, 170 and 252 can basically comprise any amino acid exchange that leads to stabilization, e.g. an increase in the thermal or hydrolytic stability, of the wild-type enzyme. Preferably, the mutation in position 96 comprises an amino acid exchange of glutamic acid for glycine, whereas with respect to position 170, an amino acid exchange of glutamic acid for arginine or lysine, in particular an amino acid exchange of glutamic acid for lysine, is preferred. Regarding the mutation in position 252, this preferably comprises an amino acid exchange of lysine for leucine.

The mutated glucose dehydrogenase can be obtained by mutation of a wild-type glucose dehydrogenase derived from any biological source, wherein the term "biological source" in the sense of this invention comprises both prokaryotes, for example bacteria, and eukaryotes, for example mammals and other animals. Preferably the wild-type glucose dehydrogenase is derived from a bacterium, especially preferably a glucose dehydrogenase from *Bacillus megaterium, Bacillus subtilis* or *Bacillus thuringiensis*, in particular from *Bacillus subtilis*.

In an especially preferred embodiment of the present invention, the mutated glucose dehydrogenase is a glucose dehydrogenase obtained by mutation of wild-type glucose dehydrogenase from *Bacillus subtilis*, which has the amino acid sequence shown in SEQ ID NO: 1 (GlucDH_E96G_E170K) or in SEQ ID NO: 2 (GlucDH_E170K_$K_{252}$L).

The stable coenzyme is preferably a coenzyme that is chemically altered relative to the native coenzyme, which has a higher stability (e.g. hydrolytic stability) compared to the native coenzyme. Preferably the stable coenzyme is stable to hydrolysis under test conditions. Compared to the native coenzyme, the stable coenzyme can have a reduced binding constant for the enzyme, for example a binding constant reduced by a factor of 2 or more.

Preferred examples of stable coenzymes are stable derivatives of nicotinamide-adenine dinucleotide (NAD/NADH) or nicotinamide-adenine dinucleotide phosphate (NADP/NADPH), or shortened NAD derivatives, e.g. without AMP part or with non-nucleoside residues, e.g. hydrophobic residues. The compound of formula (I) is also preferred as stable coenzyme in the sense of the present invention.

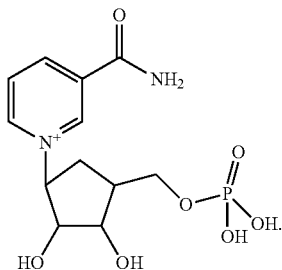
(I)

Preferred stable derivatives of NAD/NADH or NADP/NADPH are described in the references cited previously, whose disclosure is hereby expressly referred to. Especially preferred stabilized coenzymes are described in WO 2007/012494 (see also, US 2008/0213809) or U.S. Pat. No. 7,553,615, whose disclosures are hereby expressly referred to. The stable coenzyme is especially preferably selected from compounds with general formula (II):

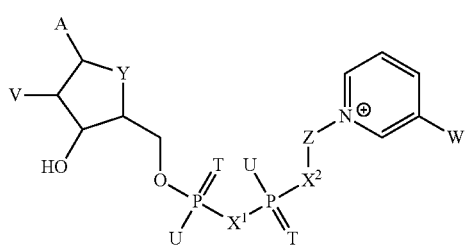
(II)

with
A=adenine or an analog thereof,
T=in each case independently O, S,
U=in each case independently OH, SH, $BH_3^-$, $BCNH_2^-$,
V=in each case independently OH or a phosphate group, or two groups that form a cyclic phosphate group;
W=COOR, $CON(R)_2$, COR, $CSN(R)_2$ with R=in each case independently H or $C_1$-$C_2$-alkyl,
$X^1$, $X^2$=in each case independently O, $CH_2$, $CHCH_3$, $C(CH_3)_2$, NH, $NCH_3$,
Y=NH, S, O, $CH_2$,
Z=a linear or cyclic organic residue,
  with the proviso that Z and the pyridine residue are not linked by a glycoside compound, or a salt or optionally a reduced form thereof.

In the compounds of formula (II), Z is preferably a linear residue with 4-6 carbon atoms, preferably 4 carbon atoms, in which 1 or 2 carbon atoms are optionally replaced by one or more heteroatoms selected from O, S and N, or a residue comprising a cyclic group with 5 or 6 carbon atoms, which optionally contains a heteroatom selected from O, S and N and optionally one or more substituents, and a residue $CR^4_2$, wherein $CR^4_2$ is bound to the cyclic group and to $X^2$, with $R^4$=in each case independently H, F, Cl, $CH^3$.

Especially preferably, Z is a saturated or unsaturated carbocyclic or heterocyclic five-membered ring, in particular a compound of general formula (III)

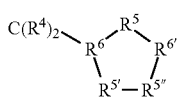
(III)

wherein there can be a single or double bond between $R^{5\prime}$ and $R^{5\prime\prime}$, with
$R^4$=in each case independently H, F, Cl, $CH_3$,
$R^5$=$CR^4_2$,
wherein $R^{5\prime}$=O, S, NH, $NC_1$-$C_2$-alkyl, $CR^4_2$, CHOH, $CHOCH_3$, and
$R^{5\prime\prime}$=$CR^4_2$, CHOH, $CHOCH_3$, when there is a single bond between $R^{5\prime}$ and $R^{5\prime\prime}$, and wherein $R^{5\prime}$=$R^{5\prime\prime}$=$CR^4$, when there is a double bond between $R^{5\prime}$ and $R^{5\prime\prime}$, and
$R^6$, $R^{6\prime}$=in each case independently CH or $CCH_3$.

In a preferred embodiment the compounds according to the invention contain adenine or adenine analogs, such as e.g. C8- and N6-substituted adenine, deaza variants such as 7-deaza, aza variants such as 8-aza or combinations such as 7-deaza or 8-aza or carbocyclic analogs, such as formycin, wherein the 7-deaza variants can be substituted in the 7-position with halogen, $C_1$-$C_6$ alkynyl, alkenyl or alkyl.

In another preferred embodiment the compounds contain adenosine analogs, which instead of ribose contain e.g. 2-methoxy-deoxyribose, 2'-fluoro-deoxyribose, hexitol, altritol or polycyclic analogs, such as bicyclo-, LNA- and tricyclo-sugars.

In particular, in the compounds of formula (II), (di-)-phosphate oxygens can also be replaced isotronically, such as e.g. O— by S— or $BH_3$—, O by NH, $NCH_3$ or $CH_2$ and =O by =S.

In the compounds according to the invention of formula (II), W is preferably $CONH_2$ or $COCH_3$.

In the groups of formula (III), $R_5$ is preferably $CH_2$. It is further preferred for $R_5'$ to be selected from $CH_2$, CHOH and NH. In an especially preferred embodiment $R_5'$ and $R_5''$ are each CHOH. In yet another preferred embodiment $R_5'$ is NH and $R_5''$ is $CH_2$.

In the most preferred embodiment the stable coenzyme is carbaNAD.

The preferred test chemistry is in particular designed in such a way that the enzymes it contains are long-term-stabilized. This means that the enzyme stabilized with a stable coenzyme, e.g. as dry substance, is stored for example for a period of at least 2 weeks, preferably of at least 4 weeks and especially preferably of at least 8 weeks and wherein the enzyme activity decreases preferably by less than 50%, especially preferably less than 30% and most preferably by less than 20% relative to the initial value of the enzyme activity.

Furthermore, the test chemistry can be designed in such a way that the enzyme stabilized with a stable coenzyme is stored at elevated temperatures, for example at a temperature of at least 20° C., preferably of at least 25° C. and especially preferably of at least 30° C. The enzyme activity then decreases preferably by less than 50%, especially preferably less than 30% and most preferably by less than 20% relative to its initial value.

As a result of the stabilization according to the invention it is possible to store the enzyme stabilized with a stable coenzyme even without drying reagent for a long time, as stated above, and/or at high temperatures, as given above. Furthermore, the stabilized enzyme can also be stored at a high relative air humidity, e.g. a relative air humidity of at least 50%, wherein the enzyme activity decreases preferably by less than 50%, especially preferably less than 30% and most preferably less than 20% relative to the initial value.

The storage of the enzyme stabilized with a stable coenzyme can on the one hand take place as dry substance and on the other hand in the liquid phase. Preferably the storage of the stabilized enzyme takes place on or in a test element, which is suitable for determination of an analyte. The enzyme stabilized with a stable coenzyme is then a component part of the preferred test chemistry, which can optionally contain other components such as salts, buffers, etc. Preferably the test chemistry is free of a mediator.

The enzyme stabilized with a stable coenzyme can generally be used for detecting analytes, for example parameters in body fluids such as blood, serum, plasma or urine or in wastewater samples or foods.

As analytes, any biological or chemical substances that can be detected by a redox reaction can be determined, e.g. substances that are substrates of a coenzyme-dependent enzyme or coenzyme-dependent enzymes themselves. Preferred examples of analytes are glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LDH), carbon dioxide etc. Preferably the analyte is glucose. Detection of glucose with the aid of glucose dehydrogenase (GlucDH) is especially preferred.

The alteration of the stable coenzyme through reaction with the analyte can basically be detected in any manner. Basically, all methods for detecting enzymatic reactions known from the prior art can be used. Preferably, however, the alteration of the coenzyme is detected by optical methods. Optical methods of detection comprise for example the measurement of absorption, fluorescence, circular dichroism (CD), optical rotary dispersion (ORD), refractometry etc.

An optical method of detection, which preferably finds application within the scope of the present application, is photometry. However, photometric measurement of a change of the coenzyme as a result of reaction with the analyte requires the additional presence of at least one mediator, which increases the reactivity of the reduced coenzyme and allows transfer of electrons to a suitable optical indicator or an optical indicator system.

Possible mediators, suitable for the purposes of the present invention, include nitroso anilines, for example [(4-nitrosophenyl)imino]dimethanol hydrochloride, quinones, for example phenanthrene quinones, phenanthroline quinones or benzo[h]-quinoline quinones, phenazines, for example 1-(3-carboxypropoxy)-5-ethylphenazinium trifluoromethanesulfonate, and/or diaphorase (EC 1.6.99.2). Preferred examples of phenanthroline quinones comprise 1,10-phenanthroline-5,6-quinones, 1,7-phenanthroline-5,6-quinones, 4,7-phenanthroline-5,6-quinones and N-alkylated or N,N'-dialkylated salts thereof, wherein in the case of N-alkylated or N,N'-dialkylated salts, halides, trifluoromethanesulfonate or other anions that increase solubility are preferred as counterion.

As optical indicator or as optical indicator system, it is possible to use any substance that can be reduced and, on reduction, undergoes a detectable change of its optical properties, for example color, fluorescence, remission, transmission, polarization and/or refractive index. The presence and/or the amount of the analyte in the sample can be determined with the naked eye and/or by means of a detecting device using a photometric method that appears suitable to a person skilled in the art. Heteropoly-acids, and in particular 2,18-phosphomolybdic acid, are preferably used as optical indicators, which are reduced to the corresponding heteropolyblue.

Especially preferably, the change of the coenzyme is detected by measurement of the fluorescence. Fluorescence measurement is highly sensitive and makes it possible to detect even low concentrations of the analyte in miniaturized systems.

Alternatively, the change of the coenzyme can also be detected electrochemically using a suitable test element, for example an electrochemical test strip. A precondition is once again the use of suitable mediators, which can be transformed to a reduced form by the reduced coenzyme through transfer of electrons. The analyte is determined by measuring the current required for reoxidation of the reduced mediator, which is correlated with the concentration of the analyte in the sample. Examples of mediators that can be used for electrochemical measurements comprise in particular the mediators mentioned above, used for photometric measurements.

For detecting an analyte, a liquid test can be used, wherein the reagent is for example in the form of a solution or suspension in an aqueous or nonaqueous liquid or as powder or lyophilizate. However, a dry test can also be used, wherein the reagent is applied to a carrier, a test strip. The carrier can for example comprise a test strip, comprising an absorbent and/or swellable material, which is wetted by the sample fluid to be investigated.

An especially preferred test format comprises the use of the enzyme glucose dehydrogenase with a stable NAD derivative for detecting glucose, wherein a derivative of the reduced coenzyme NADH is formed. NADH is detected by optical methods, e.g. by photometric or fluorometric determination after UV excitation. An especially preferred test system is described in US 2005/0214891, which is expressly referred to here.

The test chemistry can in particular contain an enzyme stabilized with a stable coenzyme, wherein the stabilized enzyme, on storage preferably for at least 2 weeks, especially preferably at least 4 weeks and most preferably at least 8 weeks at a temperature of preferably at least 20° C., especially preferably at least 25° C. and most preferably at least 30° C., optionally at high air humidity and without drying reagent, displays a decrease in enzymatic activity of less than 50%, preferably less than 30% and most preferably less than 20% relative to the initial value.

Other types of stable test chemistries can also be used alternatively or additionally, for example the test chemistry described in WO 2007/012494 A1. The test chemistry can basically be contained in any manner in a test element. The test chemistry and/or the test element can be suitable for carrying out dry or liquid tests. For example the test chemistry can be applied for this purpose on a suitable carrier material, for example on a plastic and/or a ceramic material and/or a paper material.

In the second aspect of the present invention, the analytical magazine has a packing density of the analytical aids of more than 5 analytical aids per $cm^3$, preferably at least 10/$cm^3$, in particular at least 16/$cm^3$, preferably at least 25/$cm^3$ and for example 32.3/$cm^3$. This packing density is also preferred in the other aspects of the present inventions. Furthermore, in this second aspect of the present invention, as well as in other aspects, the analytical magazine can preferably have one or more of the following properties: a total volume of not more than 10 $cm^3$; an outer radius of not more than 5 cm; an inner radius between 0.5 cm and 2 cm; a thickness of not more than 1 cm; a number of analytical aids from 10 to 100; a volume between 3 $cm^3$ and 30 $cm^3$.

It is especially preferable if an external volume of the analytical magazine, i.e. a volume not taking into account optional holes or other optional openings in the analytical magazine, does not exceed 5 cm$^3$, preferably 3 cm$^3$ and especially preferably 2 cm$^3$. For example the external volume can be 1.94 cm$^3$. It is especially preferable if an empty volume of the analytical magazine, i.e. a total volume of optionally present openings in the analytical magazine, does not exceed 0.8 cm$^3$, preferably 0.5 cm$^3$ and especially preferably 0.4 cm$^3$. For example, the empty volume can be 0.39 cm$^3$. The openings can for example be internal openings of a disk-shaped analytical magazine, in which for example a drive can engage. This empty volume should not include the internal space inside the housing, for example the chambers. Net volume means, within the context of the present invention, generally the external volume minus the empty volume. In the case of a circular disk-shaped magazine, we therefore have a volume that can be found essentially from the diameter and the height of the circular disk, and in the case of an annular magazine, a net volume that is found, relative to the net volume of a corresponding circular disk, by deducting the volume of a central recess. Accordingly it is preferable if the net volume of the analytical magazine, i.e. the external volume minus the empty volume, does not exceed 5 cm$^3$, especially preferably 3 cm$^3$ and in particular 2 cm$^3$. For example, the net volume can be 1.55 cm$^3$.

Packing density generally means, within the context of the present invention, a number of analytical aids per net volume of the analytical magazine. As described above, each analytical aid can, however, comprise several partial aids, which can interact with one another, for example in each case as a test. Preferably each analytical aid comprises, as partial aids, a test element with at least one test chemistry. Additionally each analytical aid can comprise, as further partial aids, at least one lancet, which serves for sample generation of a sample of body fluid, which is then applied on the associated test element. If several analytical partial aids are contained in an analytical aid, for calculation of the packing density, associated analytical partial aids still count as analytical aids, for example a test element and an accompanying lancet are counted as a joint analytical aid. For example, in each case exactly one analytical aid with at least one test element and optionally at least one lancet can be accommodated in one chamber in each case. As described above, however, other embodiments are also possible.

Thus, the analytical magazine can be designed for example as a circular disk, with an outside diameter of less than 100 mm, for example 50 mm, and an inside diameter of a recess of the circular disk of less than 50 mm, for example 22.5 mm. The analytical magazine can for example have a thickness of less than 5.0 mm, for example a thickness of 3.1 mm. The analytical magazine can preferably comprise more than 20 analytical aids, for example at least 50 analytical aids and even 100 analytical aids or more. For example, 50 analytical aids can in each case be provided with a test element and optionally in each case additionally a lancet, wherein in each case a test element and an accompanying lancet count as one analytical aid, also called "test". For example, in each case one such analytical aid can be accommodated in one chamber in each case. Accordingly the packing density can for example be at least 50 analytical aids/5 cm$^3$=1 analytical aid/0.1 cm$^3$, preferably at least 50 analytical aids/3 cm$^3$=1 analytical aid/0.06 cm$^3$ and especially preferably at least 50 analytical aids/2 cm$^3$=1 analytical aid/0.04 cm$^3$. For example, the packing density can be 50 analytical aids/1.55 cm$^3$=1 analytical aid/0.031 cm$^3$. However, a design of the analytical magazine other than a design as a circular disk is possible, for example in one or more of the geometries described above. A design as belt magazine is for example possible, wherein for example one chamber of the belt magazine comprises a "good reel" with still unused analytical aids and another chamber of the belt magazine comprises a "bad reel", on which analytical aids that have already been used can be accommodated.

When a stable test chemistry is used, basically a moisture-impervious design of the separation of the individual chambers can even be dispensed with completely. In a third, also subordinate aspect of the present invention, which can be implemented individually or also in combination with the aforementioned first aspect and/or the aforementioned second aspect in one or more of the embodiments described, but can also be implemented independently, therefore once again an analytical magazine is proposed, which can in particular, but not necessarily, be designed according to one or more of the embodiments described above. Other embodiments are, however, also possible, in particular embodiments in which the analytical magazine is not designed according to the first aspect as a reversing magazine or as a magazine with two possible orientations and/or embodiments in which the dimensioning is not as stated in the second aspect. For preferred embodiments of the analytical magazine according to the third aspect of the present invention, once again reference may be made to the above description of the preferred additional features of the first aspect and of the second aspect. These additional features can also be implemented independently of the other features of the first aspect and/or of the second aspect within the scope of the third aspect of the present invention.

The analytical magazine has, in the third aspect of the present invention, once again at least two chambers, in which analytical aids can be accommodated. The analytical aids are accommodated in at least one of the chambers. The analytical aids comprise in each case at least one test element with at least one test chemistry for detecting at least one analyte in a liquid sample, in particular a body fluid. The test chemistry is once again designed in such a way that it is at least largely stable against environmental effects, in particular against moisture. In this third aspect of the invention it is proposed to construct the chambers separately from one another in such a way that an exchange of moisture between the chambers, for example between adjacent chambers, is possible. For example, the chambers can have chamber walls, wherein slots or other openings are provided in or next to the chamber walls, preferably with a width of opening of not more than 20 micrometers, in particular of not more than 10 micrometers. These widths of opening allow, on the one hand, an exchange of air humidity between the chambers, but as a rule hold back coarser contaminants or germs. Alternatively or additionally, materials can be used for the walls of the chambers and/or the housing which are permeable to water vapor. In this third aspect of the present invention, the analytical magazine, in particular at least one of the chambers of the analytical magazine, is arranged for remagazining the analytical aids or partial aids of these analytical aids again in at least one of the chambers after use. Regarding the term remagazining and the possible embodiments of the analytical magazine for the purpose of remagazining, reference may be made to the above description of the first aspect of the invention. In particular, once again holding elements can be provided, for holding an analytical aid or, which is equivalent within the context of this aspect, a partial aid such as for example a lancet or a microsampler, for example positively and/or nonpositively in an opened chamber after remagazining. In the case of remagazining, the test chemistry that is at least largely stable against environmental effects proves particularly advantageous, because in many cases moisture, for example in the form of a liquid sample, is actively brought into the chamber during remagazining. The use, according to the invention, of the test chemistry that is stable against environmental effects can avoid these problems compared with conventional test chemistries.

The second aspect described above and/or the third aspect described above of the invention, as well as the first aspect of the invention described above, can have various advantageous further embodiments.

In particular, as described above, an analytical aid can in each case comprise one test element with one test chemistry, in particular the test chemistry that is stable against environmental effects, and one lancet. These partial aids can be stored together in one and the same chamber, for example in each case a pair consisting of one lancet and one test element in one chamber, or several such pairs in a common chamber. By using the test chemistry that is stable against environmental effects, in particular air humidity and/or beta radiation, a primary requirement of separate packaging of lancets and test elements is unnecessary. Furthermore, there is also no need to provide moisture-proof packaging of the test chemistry and/or to insert a drying agent in the chambers and/or the analytical magazine. Therefore new concepts are possible, in particular for a combined analytical magazine with lancets and test elements. It is unnecessary to keep the lancets and the test elements separate from one another. Moreover, as explained in more detail below, other materials can be considered for the magazine parts, as the requirements for radiation stability and moisture-proof properties no longer have to be fulfilled simultaneously.

As it is possible to dispense with a barrier between the analytical aids, in particular between lancets and test elements, the lancet elements and test elements can be arranged far more compactly, for example in the same chamber of the analytical magazine. During storage in the chamber, the point of the lancet can for example be right next to the test chemistry, which after sample acquisition is also suitable as position for transfer of the sample to the test chemistry. As a result, a mechanism for actuating the analytical aids can be of much simpler design than with the usual analytical magazines, because for example an additional movement for removing a second barrier, such as a barrier between lancet and test element, is no longer required and because the lancet does not have to be moved to an additional position. In contrast to existing concepts with separate packaging of lancet and test chemistry, the test chemistry does not necessarily have to be moved, in order to remove it from its packaging. In this case, as a rule only the lancet has to be docked on a corresponding actuator and moved.

High packing densities can be achieved in particular by storing the analytical aids very close together, without having to provide hermetic separation between the analytical aids. In this respect, the use of the stable test chemistry proves especially advantageous. Thus, it is possible for example to use analytical magazines that have a housing with a wall thickness of max. 1.2 mm. The wall thickness is to be understood as the thickness of the housing between a chamber comprising an analytical aid and the surroundings or an adjacent chamber, in particular at a thinnest point of the housing. It is especially preferred if the wall thickness is not more than 1.0 mm and in particular not more than 0.8 mm. For example, the wall thickness can be selected between 0.3 mm and 0.8 mm.

Once again alternatively or additionally, it is not necessary to use a drying agent such as activated charcoal for example in the analytical magazine. Accordingly, it is especially preferable if the analytical magazine is designed to be free from drying agent. In this way there is also a saving of space. A drying agent is then generally to be understood as a substance that is capable of absorbing a quite large amount of water, for example an essentially preferably water-absorbing substance. In usual analytical magazines at least one chamber is provided with a drying agent. According to the invention, however, an analytical magazine can be provided in which, in the unused state, there are exclusively sealed chambers with analytical aids, but not an opened chamber with a drying agent.

Furthermore, in particular when using a test chemistry that is at least largely stable against environmental effects, it is also possible to employ better and more accurate joining techniques for making the housing. Thus, it is especially preferable, as explained in more detail below, if the analytical magazine has a housing with at least two parts, in particular at least two magazine halves. The two parts need not necessarily be of identical design. The housing, in particular the at least two parts together, can form the at least two chambers. It is especially preferable if the at least two parts are joined together by a method without the use of an adhesive. In particular, integral joining methods without adhesive are suitable. The use of at least one laser welding process is especially preferred, based on the high precision and little formation of contaminants. With a laser welding process it is possible to achieve uniform weld seams with a small width and high precision, wherein the process offers good thermal control and localization simultaneously and can be performed virtually without contamination.

Especially when using a laser welding process, it is possible to make the first of the at least two parts of transparent design and the second of the at least two parts absorbent. The at least two parts can preferably have the same basic material, but each with a different absorption for light in the visible and/or infrared and/or ultraviolet region of the spectrum. For example, the at least two parts can have a different absorption in a region of the spectrum between 500 and 1200 nm, in particular in a region of the spectrum from 700 to 1100 nm or 700 to 1000 nm, in which usual lasers employed for laser welding emit, for example semiconductor lasers and/or Nd:YAG lasers. To achieve a different transparency and/or absorption of the at least two parts, a basic material of the parts can be colored differently, for example by adding a colorant to the basic material (for example polycarbonate, PC) of one of the parts, to reduce the transparency.

If a welding process is used for joining the at least two parts, generally the weld seams can for example have a width of max. 0.5 mm, in particular of max. 0.3 mm and especially preferably of max. 0.2 mm. This also contributes to the increase in packing density. In particular, once again it proves advantageous if the test chemistry is at least largely stable against environmental effects, as in this case a transfer of moisture from one chamber to another chamber is largely irrelevant.

Generally, a large number of materials can be used for the housing, in particular for the at least two parts of the housing, for example for the two magazine halves. In particular, thermoplastics can be used. However, a particular advantage of the invention, in particular when using a test chemistry that is at least largely stable against environmental effects, is that these plastics do not have to fulfill any special requirements with respect to impermeability to moisture. For example, it is also possible to use materials that are permeable to water vapor. Accordingly, selection and design of the plastics can for example be based on other criteria, for example processability in a particular forming process, for example in injection molding. It is also possible to use less expensive materials. For example, one or more of the following plastics can be used: PC (polycarbonate); ABS (acrylonitrile-butadiene-styrene); COC (cyclo-olefin copolymers); PMMA (polymethylmethacrylate); PS (polystyrene); PET (polyethylene terephthalate). These materials have advantages with respect to their processing properties and/or with respect to their costs, but basically cannot easily be used if they must also meet the requirement of being vapor-proof.

PC for example has a high resistance to ionizing radiation and a high transparency over a wide region of the spectrum. It is an inexpensive mass-produced material, which however has a comparatively high permeability to water vapor. However, as this permeability is basically largely irrelevant within the context of the present invention, in particular when using the stable test chemistry, and as the processing properties of this material are particularly good in practice, this material is especially preferred within the scope of the present invention.

ABS has very good processing properties and in particular very good injection molding properties, so that the use of this material is also advantageous. This material also has a comparatively good transparency for a wide region of the spectrum, and low costs.

COC does have high transparency in a wide region of the spectrum from the ultraviolet to the infrared and provides a good vapor barrier, but is comparatively expensive and is only moderately stable to excessively ionizing radiation.

PMMA has little or no natural fluorescence in the ultraviolet region of the spectrum and has good transparency for a wide region of the spectrum. The high vapor permeability of this material is tolerable within the scope of the present invention, in particular when using the stable test chemistry, and it is a less expensive material. Therefore this material too can be used advantageously within the scope of the present invention.

PS processes well, especially in injection molding. It has good transparency for a wide region of the spectrum. Moreover, it is a less expensive, mass-produced plastic. Thus, on the whole, this material is suitable for use within the scope of the present invention.

With this extended selection of materials, which is no longer restricted by the requirement for impermeability to vapor, it is basically possible to join the preferably at least two parts of the housing of the analytical magazine by laser welding, instead of a conventional ultrasonic welding and/or a method using adhesive, which would remain for nontransparent materials. Similar materials can for example be welded very easily using a laser, for example PC to PC and/or COC to COC etc., especially when a part is light absorbent for the laser wavelength, for example owing to a corresponding coloration and/or doping, and wherein the other part is transparent or more transparent. Basically, opaque parts can also be irradiated so that welding is possible, but the weld seams are then as a rule coarser and take up more space. However, with high transparency and smooth surfaces of the parts to be joined together, very narrow weld seams can be achieved, for example weld seams with the aforementioned width of 0.3 mm. These small weld seams allow the analytical magazine to be of very small design, for example with the preferred packing densities described above. Moreover, formation of dust, which usually occurs in other welding processes, for example in ultrasonic welding, can be avoided in laser welding. Furthermore, there are no vibrations, which could cause structures or parts of the analytical magazine to resonate. Also, no added materials are required, for example adhesives, which might contaminant the interior of the chambers and/or the analytical aids, so that for example hydrophilicity of lancets or microsamplers would be jeopardized.

Also, in particular by using laser welding and/or the preferred plastics, new methods are possible for closing and/or sealing the analytical magazine, for example for sealing a finished analytical magazine. Until now, in many cases analytical magazines have been sealed thermally with heat-sealable films. However, the hot-melt adhesives that are used can in some circumstances affect the analytical aids. For example, vapors of the hot-melt adhesive can affect lancets and/or microsamplers, for example impair their hydrophilicity. However, by means of the proposed invention, in particular using the laser welding process and/or the proposed materials, it is possible, alternatively or additionally to for example metal foils, e.g. aluminum foil, to use one or more plastic films for sealing the analytical magazine, which for example can be welded-on using a laser, instead of being glued on.

Overall, the newly obtained freedom in the selection of materials therefore offers a basis for a far more compact system. This is not only because the analytical magazine can be designed with a much smaller space and/or a much higher packing density. The analytical magazine can also be designed so that its production and/or its operation are greatly simplified and less expensive.

As shown above, alongside the analytical magazine in one or more of the embodiments described above, an analytical system is also proposed for detecting at least one analyte in a body fluid. The analytical system can for example be the aforementioned measuring system or can comprise a measuring system of this kind. The analytical system is arranged to receive at least one analytical magazine in at least two different orientations. The analytical magazine can in particular be designed according to one or more of the embodiments described above.

However, the feature of the analytical magazine described above, that it is arranged to hold the analytical aids in place in the chambers after remagazining, is not necessarily required within the scope of the proposed analytical system, instead the analytical system can also be designed so that the analytical magazine does not hold the analytical aids in place in the chambers after remagazining. Holding in the chambers after remagazining, for example by means of a force closure, in particular a frictional closure, can in this case be dispensed with, even if such holding is still preferred. If no such holding is provided, the analytical aids can be retained in the chambers for example by components of the analytical system, for example walls of a receiver for the analytical magazine.

The analytical system can for example have a receiver, into which the analytical magazine can be received in the at least two orientations. As described above, the analytical system can for example provide at least one interface, for example an interface with mechanical and/or electrical and/or optical functions, wherein for example the same interface can interact with the various partial magazines in the different orientations, for example in each case with the partial magazine which, in the current orientation of the analytical magazine, is located in an application position or application orientation and, in the current orientation, can supply analytical aids to the analytical magazine. As described above, the mechanical interface can for example bring about further indexing of the analytical magazine and/or provide at least one actuator for coupling to the analytical aid that is located in the application position and/or provide a measuring system for performing a measurement with a test element of the analytical aid that is located in the application position or application level. Reference may be made to the above description regarding other possible embodiments of the analytical system and/or of the analytical magazine.

The analytical system can furthermore be arranged to execute at least one sampling movement, by means of the analytical aids received in the analytical magazine. The analytical system is furthermore arranged to execute a remagazining of the analytical aids. For example, the analytical system can be arranged so that first it is coupled to an analytical aid located in an application position, which can also comprise a partial aid, with which it performs a sampling movement, then executing a remagazining and then once again uncoupling from said analytical aid. Reference may be made to the above description for further embodiments and options.

The analytical system can in particular have at least one application position and/or application level. An application position or application level is to be understood as a position or level, in which at least one chamber of the analytical magazine can be provided, so that said chamber and/or the analytical aid received in said chamber can be used for analytical detection, for example the sampling movement and/or the analysis of the sample. As explained above, several application positions can also be provided, for example several application positions in one application level. For example, as described above, the sampling movement and the measurement of the sample can take place at different locations.

The analytical system can in particular be arranged so that, in at least two different orientations of the analytical magazine, it accesses at least one chamber and/or at least one analytical aid in the application position and detects the at least one analyte by means of said chamber and/or by means of the analytical aid in the application position. For example, coupling can take place for a sampling movement and/or a remagazining and/or coupling for measuring purposes, for example by means of an electrical measurement and/or an optical measurement or similar measurements, which can for example be adapted to the type and mode of operation of the test chemistry.

It has already been explained that the analytical magazine can in particular be designed so that it comprises at least one indicating element, which can supply the analytical system with at least one piece of information about a current orientation. The analytical system can be equipped correspondingly, to acquire one or more of the following data: An orientation of the analytical magazine; a number of analytical aids of the analytical magazine already used in the current orientation; a number of aids of the analytical magazine still remaining in the current orientation; information about orientations of the analytical magazine that have already been used; information about orientations of the analytical magazine still remaining. Said acquisition can for example take place by means of one or more of the indicating elements described above. The at least one indicating element can for example be designed as nonvariable, for example by means of corresponding rigid elements, which indicate an orientation. Alternatively or additionally, however, at least one indicating element can also be provided, which is designed as variable, for example in the form of a variable mechanical and/or electronic information carrier. In this way, for example before and/or after each use of a chamber and/or of an analytical aid, the indicating element, which acts as information carrier, can be altered, for example in order to update an information of the kind described above. Various examples of implementation are described below in more detail. Moreover, the analytical system can in particular be arranged so that it communicates the at least one piece of information of the stated kind to a user, for example by means of an optical and/or acoustic and/or haptic indication.

The analytical system can in particular be arranged to request a user to change an orientation of the analytical magazine. The change of orientation can for example take place automatically. However, a manual change of the orientation is especially preferred. The analytical system can in particular, for example based on the at least one piece of information described above, recognize that no unused analytical aids are available in a current orientation. Correspondingly, the analytical system can for example request a user to change the orientation of the analytical magazine, for example by opening a system housing of the analytical system, taking out the analytical magazine, turning it round and reinserting it into the housing.

The analytical magazine and the analytical system according to one or more of the embodiments described above have a number of advantages over known analytical magazines and known analytical systems. Thus, in particular, analytical systems can be designed which satisfy the integration concept described, in which at least two system functions are combined. In particular, the system functions of sampling and sample analysis can be performed by one and the same analytical magazine. However, at the same time, according to the invention, the requirements described are fulfilled well, in particular the requirements for a microsampler magazine. Thus, analytes can be detected qualitatively and/or quantitatively within the magazine, for example optically and/or electrochemically. At the same time, based on a possible introduction of a test chemistry inside the chambers, stability of the test chemistry can be guaranteed. As the test chemistries are preferably each arranged in different chambers, cross-contaminations between individual micro samplers can be avoided.

At the same time, the aforementioned analytical magazines can be of simple and inexpensive design. Furthermore, an especially compact form of magazining can be provided, for example by means of a double form of housing. The compact form of magazining makes it possible, for example, to magazine analytical aids, in particular disposables, above one another. For example, in the case of magazining in a disk magazine, a radius of the disk can be intended for 25 analytical aids. Based on a double form of housing, however, magazining of 50 disposables is possible, for example while using a correspondingly smaller or constant diameter of the disk. After consumption of the 25 disposables, a user can accordingly be requested to take out the analytical magazine and turn it over. An interface on the equipment, which allows the system to be coupled to the analytical magazine, can remain the same for all analytical aids, for example for all 50 analytical aids.

This constancy of an optional interface of the analytical system, which serves for coupling the analytical magazine and/or the analytical aids to the analytical system, offers a great many advantages. These advantages are obtained in particular when using the stated microsamplers, with which for example a measurement of the test field can take place after a remagazining in the magazine housing. As a rule such systems require precise positioning of the analytical aids that are received, for example fixed, in the magazine housing, for example the test elements, relative to a measuring system, for example an optical measuring system. Moreover, this positioning must always be provided reproducibly. Based on the use of the analytical magazine according to the invention, for example the reversing magazine described above, these interfaces and/or the at least one measuring system can, however, be of identical design for all orientations and/or can remain unaltered in the analytical system, in particular for all analytical aids. This offers particular advantages, especially for analytical systems that are based on remagazining.

DRAWINGS

Further details and features of the invention can be seen from the following description of preferred examples of implementation. The various features can be implemented individually or several in combination with one another. The invention is not limited to the examples of implementation. The examples of implementation are shown schematically in the figures. The same reference numbers in the individual figures designate elements that are identical or functionally identical or that correspond to one another with respect to their function.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
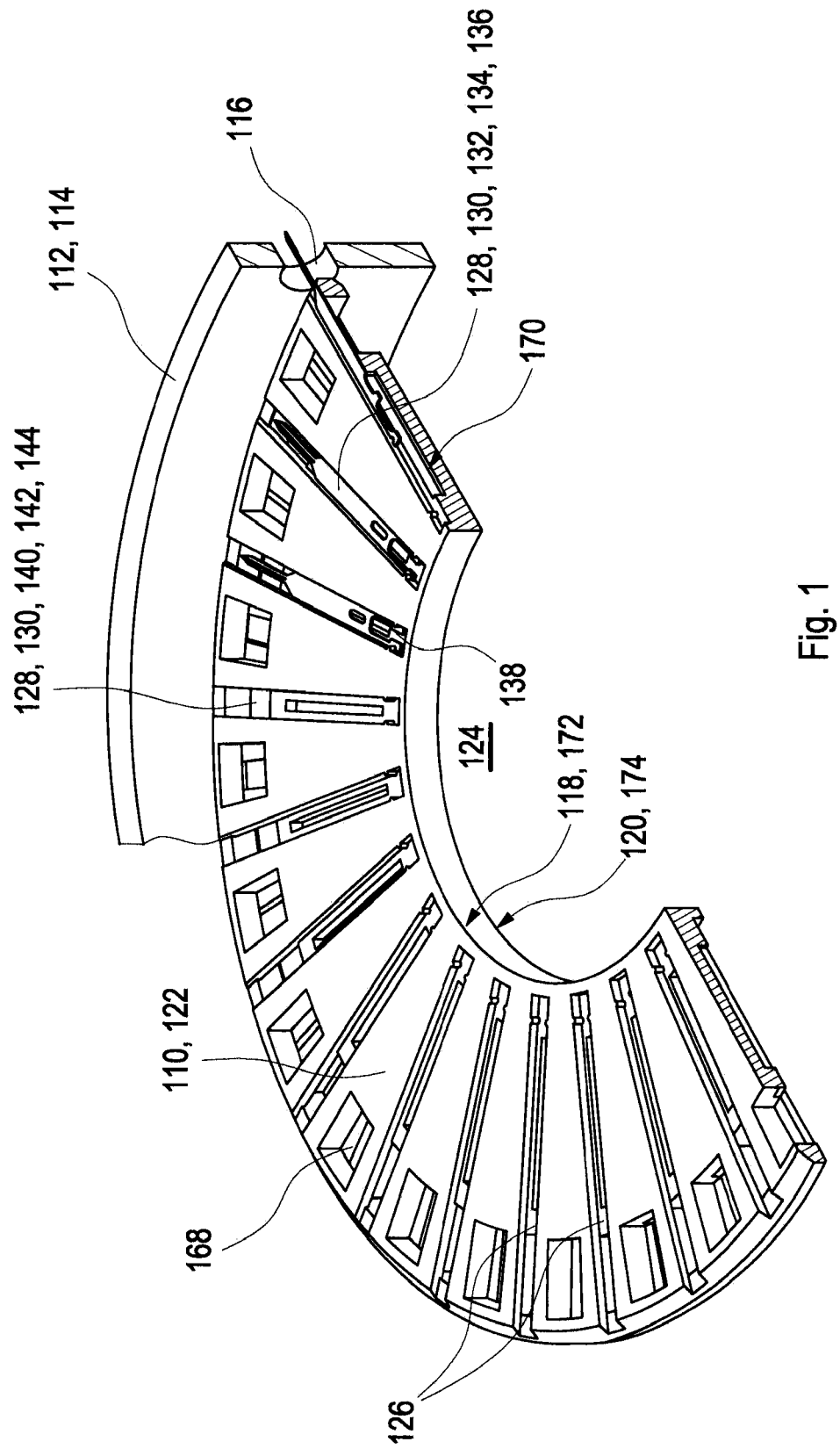
FIG. 1 shows a first example of implementation of an analytical magazine according to the invention in the form of a disk magazine.

FIG. 1 shows a first example of implementation of an analytical magazine according to the invention 110 in a perspective sectional view. The analytical magazine 110 is, as explained below, designed for example as a reversing magazine according to the first aspect of the present invention. Independently of this embodiment, the analytical magazine 110 according to FIG. 1 can also serve as example of implementation for the second and third aspect of the present invention.

The representation in FIG. 1 shows furthermore a part of a housing 112 of an analytical system 114, with a finger opening 116, through which a sampling movement can take place. The analytical magazine 110 is, in the example of implementation shown, designed as reversing magazine in the form of a round disk magazine and has two levels of aids 118, 120. These two levels of aids 118, 120 are in each case arranged parallel above one another and are parallel to the plane of the disk of the analytical magazine 110. The analytical magazine 110 has a housing 122 with a large, round central opening 124. The housing 122 accommodates, in each level of aids 118, 120, a plurality of chambers 126. In the example of implementation shown, the chambers 126 are arranged radially and equidistantly in the housing 122. In the representation according to FIG. 1, the housing 122 is shown opened, so that the chambers 126 of the first level of aids 118 face upward and are open. The chambers 126 of the second level of aids 120 are in each case located, rotated by a half unit, below the chambers 126 of the first level of aids 118. The analytical magazine 110 can thus be composed of two identical half-levels, which are mounted opposite one another and in each case are rotated relative to one another by a half unit, i.e. half the angular distance of the chamber 126.

The chambers 126, in the example of implementation shown, accommodate analytical aids 128. These analytical aids 128 are composed in each case from partial aids 130. A first partial aid 130 comprises, per chamber 126, in each case a microsampler 132 stored radially in the chambers 126. Each microsampler 132 comprises in its turn a lancet 134 and a capillary element 136 running radially inward from the lancet 134. At their end opposite the central opening 124, the microsamplers 132 each have coupling elements 138, which in the example of implementation shown are constructed in the form of loops, into which an actuator (not shown in FIG. 1) of the analytical system 114 can engage, in order to execute a sampling movement.

The chambers 126 are of radially curved design. The microsampler 132 stored in the chambers 126 are therefore curved about an axis perpendicular to their longitudinal extension and parallel to the plane of the analytical magazine 110. The microsamplers 132 are preferably, as explained in more detail below, made of a metallic material, for example sheet metal. As a result, the microsamplers 132 have a certain flexibility and, on being bent, are pressed by their restoring forces against the walls of the chambers 126. This produces a frictional closure, which holds the microsamplers 132 in the chambers 126 and which, for a sampling movement explained in more detail below, must be overcome by an actuator of the analytical system 114. After a remagazining, also explained in more detail below, the microsamplers 132 are again held in place in the chambers 126 by the frictional closure. As described above, other holding mechanisms can also be used, alternatively or additionally. The holding provided with respect to the analytical magazine according to the invention 110, which is, however, optional with respect to the analytical system 114, offers in particular the advantage that analytical aids 128 and/or partial aids, for example the microsamplers 132, cannot fall out of the chambers 126 after remagazining, which could for example lead to a risk of infection, to hygienic problems or to safety problems.

Furthermore, the analytical aids 128 have, in the example of implementation shown, in each case a test element 140. This test element 140 comprises a test chemistry 142 in the form of a test field 144, which in the example of implementation shown, is integrated in the housing 122. Each test field 144 is opposite the internal space of the respective associated chamber 126. As explained in more detail below, the test field 144 can for example be produced by inserting a test field 144 in an opening in the housing 122 of the analytical magazine 110, so that its surface faces the interior of the chamber 126. For several or all chambers 126, it is even possible to use common test fields, the boundaries of which are defined in each case by the openings in the chambers 126. The test elements 140 form further partial aids 130 of the analytical aids 128.

Figure 4:
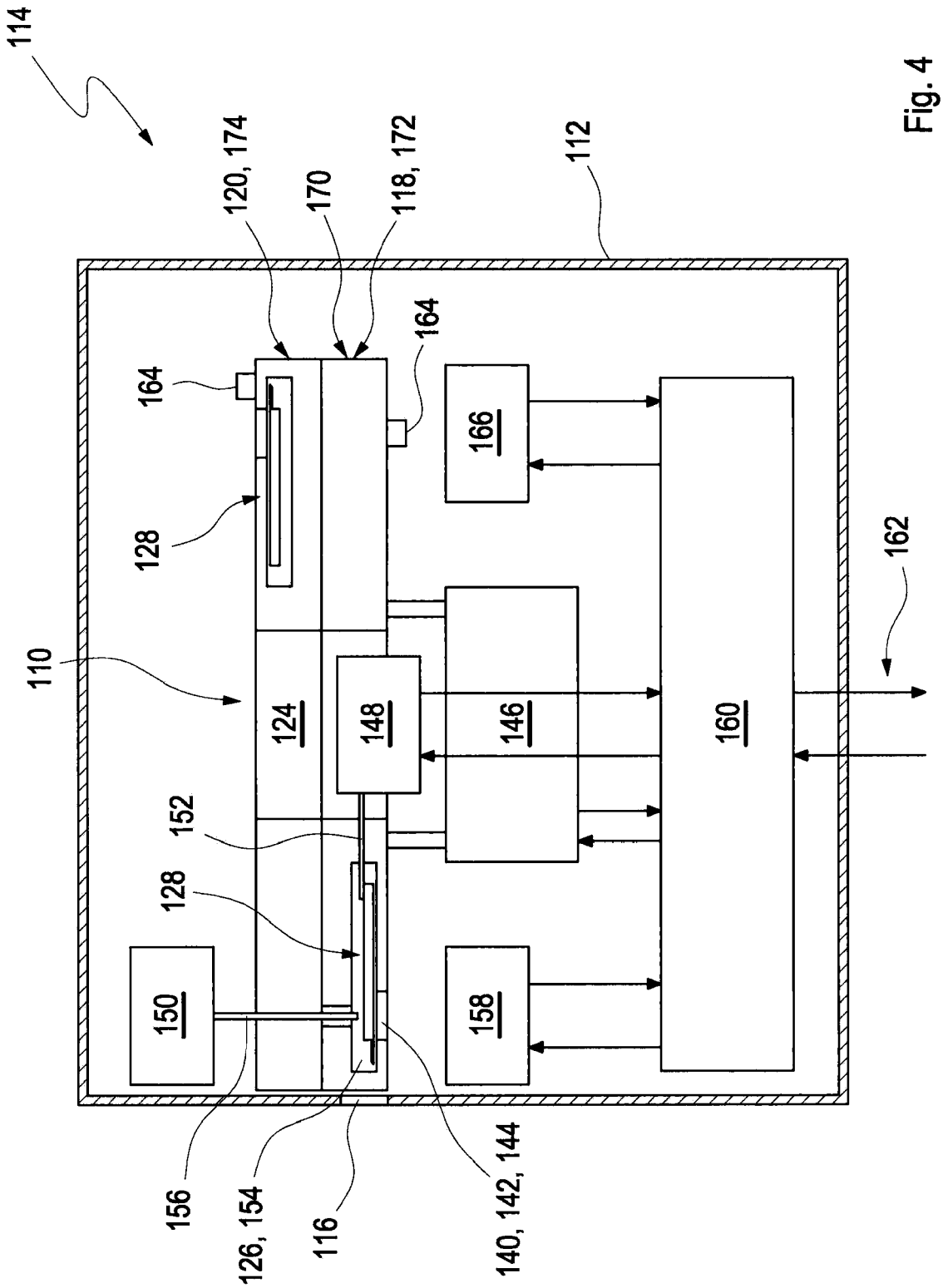
FIG. 4 shows an example of implementation of an analytical system.

The analytical system 114 is arranged to detect at least one analyte in a body fluid, by means of the analytical magazine 110 or the analytical aids 128 accommodated therein. An integrated detection takes place by means of the microsamplers 132, and will be described as an example below. Thus, FIG. 4 shows, very schematically, an analytical system 114, which accommodates an analytical magazine 110, for example according to the type shown in FIG. 1. For this purpose the analytical system 114 can have for example one or more recesses, in which the analytical magazine 110 can be accommodated in the various orientations and preferably only in these orientations. The recess can for example have at least one receiving shaft and/or at least one well and is preferably to be opened by a user from outside, in order to insert the analytical magazine 110 and/or to alter the orientation of the analytical magazine 110, for example to rotate the latter. In the case shown in FIG. 4, the analytical system 114 is arranged for using the analytical aids 128 of the first level of aids 118. The analytical system 114 can have several interfaces, in order to use the analytical magazine 110 or the analytical aids 128 located therein.

Thus, for example a positioning device 146 can be provided, which is arranged for corresponding positioning of the analytical magazine 110. This positioning device 146 can for example comprise one or more motors or the like, which can engage with corresponding transport elements of the analytical magazine 110. Furthermore, the analytical system 114 can comprise one or more actuators 148, 150, which can for example be arranged completely or partially in the central opening 124. Alternatively or additionally, further system components of the analytical system 114 can also be arranged completely or partially in said central opening 124, so that the overall size of the analytical system 114 can be reduced.

The actuators 148, 150 can for example comprise one or more actuator rods 152 and/or tappets and/or pins, which are arranged so as to couple, via the coupling elements 138, to an analytical aid 128 and/or partial aid 130 for example a microsampler 132, located in an application position 154.

An analysis cycle can for example comprise the following steps. First, by means of the positioning device 146, a new, as yet unused chamber 126 is positioned in the application position 154. Then the actuator 148 or the actuator rod 152 is coupled to the analytical aid 128 located in said chamber 126, for example by hooking of a hook of the actuator rod 152 in the loop of the coupling element 138. For this purpose, for example the actuator rod 152 can pierce a seal on the side of chamber 126 opposite the central opening 124 in the application position 154. Then a sampling movement takes place, wherein a force of the actuator 148 overcomes the frictional closure of the microsampler 132 in chamber 126, by which the microsampler 132 is held in place. Then the microsampler 132 is moved up to the finger opening 116 and through it, onto the surface of a test subject's skin. This part of the sampling movement can also be called the pricking movement. The lancet 134 of the analytical aid 128 thereby penetrates the test subject's skin and obtains a sample of blood and/or interstitial fluid. Already during penetration and/or in the penetrated state and/or during a subsequent return movement of the lancet 134, which is once again driven by the actuator 148 or the actuator rod 152, the capillary element 136 collects the sample and transports it toward the capillary, for example the capillary opening of said capillary element 136. A return movement of the microsampler 132 takes place, wherein this is remagazined in the chamber 126 in the application position 154. The microsampler 132 is once again bent by the curvature of the chamber 126 and is again pressed against the walls of chamber 126, so that the frictional closure described above is formed again and the microsampler 132 is again held in place in the chamber 126 after remagazining. Alternatively, the frictional closure can only develop after remagazining, wherein before the analytical aid 128 is used, the microsampler 132 can for example be accommodated loose in the chamber 126. In this case the position of the microsampler 132 for example after remagazining can differ from a position of the microsampler 132 before execution of the sampling movement, so that for example the curvature described above and hence the frictional closure does not occur until after remagazining.

Already during the collecting operation and/or following the collecting operation, the collected sample is transferred to the test field 144 inside the chamber 126. For this purpose, inside the chamber 126, the microsampler 132 can additionally be pressed onto the test field 144 by the second actuator 150 and/or an actuator rod 156 comprised in said actuator 150, to improve transfer of the sample onto the test field 144. Alternatively or additionally, however, this transfer can also be effected by the microsampler 132 and test field 144 simply being brought closer together, for example by a corresponding shaping of the walls of the chambers 126 and/or by a corresponding movement of the actuator rod 152. Additional openings can be provided for this purpose. The outside of the chambers 126 can additionally be sealed, to provide additional protection of the analytical aids 128 inside the chambers 126.

After the sample has been transferred to the test field 144, for example the test chemistry 142 comprised in this test field 144 can undergo a color reaction and/or some other detectable reaction, which can be detected and/or evaluated by means of a measuring system 158 of the analytical system 114. The analytical system 114 can moreover comprise other components. For example, it can contain a control system 160, which for example can control and/or evaluate the system components described. This control system 160 can for example also permit communication with a user via an interface 162, for example one or more input/output interfaces, so that a user can for example receive transmitted information and/or can operate the analytical system 114. Furthermore, the analytical magazine 110 can comprise one or more indicating elements 164, which can for example be sensed by one or more orientation sensors 166 of the analytical system 114. In this way, for example an angular position of the analytical magazine 110 can be sensed and/or an orientation of the analytical magazine 110.

The analytical magazine 110 is, as described above, designed in such a way that the analytical aids 128 in the example of implementation shown are arranged offset relative to one another in the different levels of aids 118, 120. Accordingly, as can be seen in FIG. 1, in each case a test element window 168 of one of the two levels of aids 118, 120 is positioned between two chambers 126 of the respective other one of the level of aids 118, 120. This ensures that by means of the measuring system 150 in each case, the back of the test field 144 can be observed in the application position 154, undisturbed by the adjacent chambers 126 of the respective other level of aids 118, 120. The offset arrangement of the chambers 126 thus permits access to both sides of the respective active test elements 140 in the application position 154, namely for example from one side by the measuring system 158, for example an evaluating optical system, and from the opposite side by the actuator rod 156, for example a corresponding pin, which after the entry and the sampling by the microsampler 132 can bring the latter into contact with the test chemistry 142. The other analytical aids 128 in the analytical magazine 110 are preferably not exposed and, because of their corresponding seals, remain sterile until used.

In the example of implementation according to FIG. 1, the microsamplers 132 are accommodated in the chambers 126, which can for example be constructed open at the top or bottom. This property may be important in the case of a coupling mechanism that is located outside of a magazine level. For the pricking movement, as described above, the actuator rod 152, for example an actuator tappet, can be coupled radially relative to the magazine disk of the analytical magazine 110 to the microsampler 132 and can push the latter radially forward and backward within the recess, to execute the sampling movement described above. For ensuring the storage time, the outside surface of the magazine 110 can be sealed off completely or at least partially with a thin seal, for example in the form of a thin sealing film, which for example can easily be severed for example by the actuator rod 152 and/or the lancet 134 of the microsampler 132.

The sealing film can for example also cover the test element windows 168, which act as measuring windows. In order to open these, an additional tearing mechanism can be provided, which exposes the respective test element window 168 before each measuring operation. Such a mechanism is not shown in the figures, but can be provided additionally. Said mechanism can for example become active on further indexing of the analytical magazine 110. For this, for example a retractable blade can go down into the well of the test element window 168 and push the film aside as a result of the rotation of the magazine. In another embodiment, usable alternatively or additionally, a search movement of the actuator tappet in the form of the actuator rod 152 after the coupling element 138 for example in the form of the pilot hole and/or the loop in the microsampler 132, can for example also be used for tearing the film open on its whole length, so that the actuation path is exposed beforehand. For this, for example the actuator rod 152 can pass forwards through the film, as far as the microsampler 132, and then travel backwards, until the actuator rod 152 engages in the pilot hole of the coupling element 138.

The analytical magazine 110 can for example be equipped with test elements 140 that are not sensitive to moisture, for example according to the above description from the prior art. In this case the test element windows 168, for example the measuring windows, can already be released from their film in the production process and the entire analytical magazine 119 can be placed in hermetic outer packaging, for example a plastic bag, to ensure a long shelf life. Therefore the expiry date counts from when this outer packaging is torn open by a user. Then so that the microsamplers 132 and/or other partial aids 130 of the analytical aids 128 or the analytical aids 128 as a whole are held in the chambers 126, the chambers 126 can be provided with a covering disk, which although for example overlapping the width of the microsamplers 132, nevertheless allows or facilitates engagement of the actuator rod 152.

Furthermore, insertion aids can be provided on the analytical magazine 110, which can also be combined completely or partially for example with the indicating elements 164. These insertion aids can make correct insertion of the analytical magazine 110, designed as a reversing magazine, easier for the customer. Solutions known from the prior art can for example be used for this, for example positioning holes, positioning recesses, positioning pegs and/or combinations of the aforesaid and/or other elements, which will not be discussed further here.

Generally it should be pointed out that the analytical magazine 110 can also be made without the indicating elements 164 or with fixed or variable indicating elements 164 of some other design. For example, since a drive motor can be provided in the analytical system 114, which indexes the analytical magazine 110, it is possible for example, alternatively or additionally to the use of an indicating element 164, to provide a count of the indexings, information about test operations already carried out and/or tests still remaining. Detection of an orientation of the analytical magazine 110 already used is for example also conceivable using a sensor mounted on the equipment, in particular a light barrier or a similar sensor.

Once again alternatively or additionally, the indicating element 164 also offers the possibility of new uses of the analytical magazine 110. For example, a user can also remove the analytical magazine 110 from the analytical system 114 for a while, for example for a short break in order to prepare and/or insert a sufficient number of fresh analytical aids 128, for example test elements 140. In this case the analytical system 114 could, via the variable indicating element 164, which in this case can for example operate as a variable mechanical and/or electronic information carrier, supply the analytical magazine 110 and/or the analytical system 114 with status information. On reinserting the previously used analytical magazine 110 in the analytical system 114, this status information could first be read off and the analytical magazine 110 could be brought by means of the indicating element 164 to the position of the next fresh analytical aid 128, for example the next fresh test element 140.

The analytical magazine 110 shown in FIG. 1, in the example of implementation shown, comprises two essentially identical magazine halves or consists of two essentially identical magazine halves, which by turning the magazine round with the analytical system 114 can be engaged one after another. Although reversing magazines occupy a similar construction volume as linearly enlarged magazines, the compact geometry allows a smaller and/or more ergonomic design of the analytical system 114, which for example can be designed as a measuring instrument. For example, it is possible in this way to achieve volumes of less than 130 ml. Moreover, analytical magazines 110 with a loading of 50 analytical aids 128 or more are achievable.

A user can insert the analytical magazine 110 into the analytical system 114 for example according to a mark, for example a printed mark, in particular an arrow mark. For example, the first level of aids 118 can be arranged in an application plane 170 first. In this orientation, the analytical aids 128 accommodated in this level of aids 118 in the analytical magazine 110 can be supplied one after another to the analytical system 114, for example in each case by further indexing of the magazine 110 about a chamber 126 by means of a transport mechanism of the analytical system 114. After a number of measurements, determined for example by the number of chambers 126 in the first level of aids 118 of the analytical magazine 110, for example 25 measurements, the capacity of this first magazine half is exhausted. The user can then, for example via the interface 162, receive system information for turning the analytical magazine 110. The user then opens the analytical system 114, for example by opening a corresponding flap or other type of opening on the housing 112. The half-used analytical magazine 110 can then be taken out and turned round. Another printed mark and/or some other mark on the back of the analytical magazine 110 can help in orientation during reinsertion.

Appropriate geometry of the analytical magazine 110 can prevent the risk of incorrect insertion. In particular, shapes are conceivable that break the magazine symmetry within the insertion plane. Moreover, it can be useful to detect the usage status of the analytical magazine 110, so that corresponding instructions can be issued to the user. For example, a number of analytical aids 128 already used $N_{used}$ may be important. Moreover, alternatively or additionally, detection of the used magazine half may be important. For example, the indicating element 164 on the analytical magazine can be utilized for this information.

For example, the control system 160 can be arranged to be programmable, for obtaining and/or evaluating such information. Generally it is possible, for example by appropriate electronic and/or software conversion, for example to introduce a mathematic switch H. For example, the remaining tests $N_{left}$ can be calculated from the information about the tests already used $N_{used}$ and the used magazine half. The following example of calculation is based on a magazine capacity of 2×25 tests:

$$N_{left} = (25 - N_{used}) + H \times 25$$

The mathematic switch H assumes the value H=0, if the second magazine half (i.e. the second level of aids 120) has been started. Otherwise H assumes the value H=1. The switch value H can be determined for example by means of a sensor, for example by means of the orientation sensor 166, which can for example read the indicating elements 164 on different sides of the analytical magazine 110. In this way it is possible for example to detect whether the second magazine half has been started or not. The orientation sensor 166 can for example search for traces of prior use on the active and/or on the inactive magazine half. Thus, the orientation sensor 166 can be arranged not only on the underside of the analytical magazine 110, as indicated in FIG. 4. Alternatively or additionally, the orientation sensor 166 can also be arranged on the opposite side, thus on the side turned away from the application plane 170 and for example search for traces of prior usage there. For example, conventional sensors, such as in particular optical sensors (for example light barriers or similar optical sensors) and/or capacitive and/or inductive sensors, are suitable for the orientation sensor. Basically, other types of sensors can also be used.

The indicating elements 164 can for example comprise variable indicating elements 164, which can for example be altered during usage. For example, a sealing film can be provided, in particular a metallic sealing film, which can be pressed in by prior usage. Then for example an incident light beam, for example a light beam emitted by the orientation sensors 166, is no longer reflected correctly. Similarly, for example measured capacitances (capacitor principle) and/or inductances (coil principle) can change, and/or simple storage elements, preferably variable storage elements, can be used, for example magnetic storage elements. Mechanical sensors and/or indicating elements 164, for example microswitches, are also suitable for detection and are basically known by a person skilled in the art.

Table 1 shows an example of the aforementioned variables H, $N_{used}$ and $N_{left}$ for various initial situations. Furthermore, possible user information is shown, which can be issued to a user, for example via the interface 162, in particular via one or more displays. However, other embodiments are also basically possible.

magazine half 174, wherein optionally a slight rotation about an axis perpendicular to these levels of aids 118, 120, still has to be supplemented with the offset angle of the two levels of aids 118, 120 (i.e. with half the angle of the equidistant angular distribution of the chambers 126).

The analytical magazine 110 designed as reversing magazine should guarantee the sterility of each analytical aid 128, in particular the sterility of each microsampler 132, up to the pricking operation. For this reason, at least the microsamplers 132 can be inserted in the chambers 126, which in particular are designed as separate chambers and preferably as germ-proof chambers. This problem can be solved with appropriate techniques for joining the individual parts of the analytical magazine 110, in particular of the housing 122 of the analytical magazine 110. In particular, it is possible to use joining techniques such as for example methods using adhesives and/or welding processes, in particular ultrasonic welding and/or laser welding. Preferably, any remaining gaps, for example gaps between adjacent chambers 126 and/or gaps in the housing 122, should have widths of not more than 10 μm, to prevent microbes passing through. Another possible problem with the analytical magazine 110 designed as a reversing magazine is to guarantee the expiry date for the packaging once opened. As a rule the above gap dimensions are not suitable for keeping moisture out of the interior of the housing 122. For this reason it is preferable to use a moisture-compatible, stable test chemistry 142 for the reversing magazine, which has now become available. For example, a test chemistry 142 known as carbaNAD-recipe can be used for optical test evaluation, which is described in WO 2007/012494 A1. Alternatively or additionally, however, basically hermetic housings 122 can be used and/or housings where the chambers 126 are sealed from one another and from the outside atmosphere with additional seals.

Figure 2:
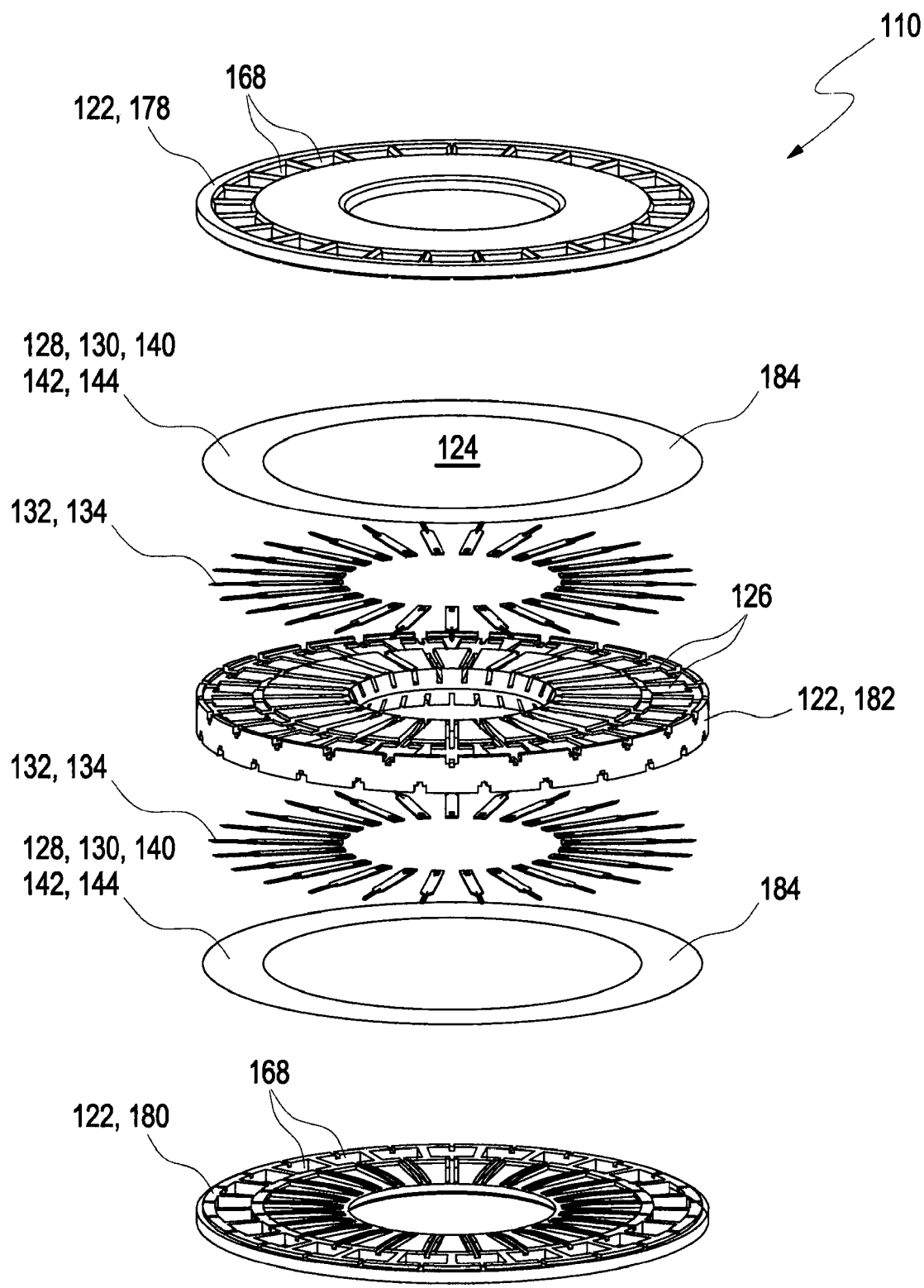
FIGS. 2A to 2D show a second example of implementation of a disk magazine according to the invention.

The analytical magazine 110 and the analytical system 114 are described above with reference to the special representation in FIG. 1. The principle shown can, however, be applied without any problem to other types of reversing magazines, for example the analytical magazines 110 in FIGS. 2A to 3, described below, which essentially differ in their external geometry. In principle, however, the technical features are

TABLE 1

Example of calculation logic for determining magazine status

| | Initial situation | H | $N_{used}$ | $N_{left}$ | User information (e.g. on a display) |
|---|---|---|---|---|---|
| 1st magazine half | New magazine inserted | 1 | 0 | 50 | New magazine detected |
| | 15 tests used | 1 | 10 | 35 | — |
| | 25 tests used | 1 | 25 | 25 | Turning of the magazine is required |
| 2nd magazine half | Magazine turned and inserted | 0 | 0 | 25 | Turned magazine detected |
| | 15 tests used | 0 | 10 | 10 | Warning, magazine nearly used up |
| | 25 tests used | 0 | 25 | 0 | Magazine replacement is necessary |

The analytical magazine 110 in the example of implementation shown in the drawings is thus designed as a reversing magazine and has two partial magazines in the form of magazine halves, which are designated hereinafter with the reference numbers 172 and 174. These magazine halves 172, 174 are essentially designed symmetrically to one another. For example, in the case of the analytical magazine 110 the first magazine half 172, after rotation about an axis parallel to the levels of aids 118, 120, makes a transition to the second interchangeable and are not linked to the special shape of magazine, so that the foregoing can apply analogously to the examples of implementation described hereunder.

Thus, FIGS. 2A to 2D show a second example of implementation of an analytical magazine according to the invention 110 in various embodiments. FIG. 2A shows an oblique perspective top view, FIG. 2B shows a top view, FIG. 2C shows a sectional view and FIG. 2D shows an exploded view of the analytical magazine 110. As can be seen from these figures, the analytical magazine 110 in the second example of implementation is also a circular reversing magazine, which essentially has the shape of a round disk.

The analytical magazine 110 is shown in the figures in the closed representation and once again has a housing 122 with individual chambers 126 (hidden in the figures by the housing 122). Regarding the individual components, reference may largely be made to the above description for FIG. 1. The chambers 126 are again distributed equidistantly in the radial orientation in the housing 122 in two levels of aids 118, 120, wherein once again there is an offset-angle by half of a distribution angle between the two levels of aids 118, 120. This can be seen in particular from the representation in FIG. 2A.

In contrast to the analytical magazine 110 according to the example of implementation shown in FIG. 1, in the example of implementation according to FIGS. 2A to 2D the microsampler 132 is not elongated in the chambers 126, but preferably is bent out of its plane at one end. The chambers 126 are in each case preferably formed from two hard components, which cause this bending. The engaging in the microsampler 132, which makes a sampling movement and remagazining possible, for example by means of the actuator rod 152, takes place by means of a hook-shaped tappet of the actuator rod 152, which enters the chamber 126 from behind, i.e. from the central opening 124. The hook-shaped tappet pushes the microsampler 132 radially outward, wherein, following the guiding contour of the chamber 126, it assumes an elongated position and so threads the pilot hole of the coupling element 138 (not shown in more detail in the figures) onto the hook-shaped tappet of the actuator rod 152. On retraction, i.e. during the return movement of the sampling movement and/or during remagazining, the microsampler 132 is again bent out of the plane and so releases the hook-shaped tappet of the actuator rod 152 again. However, other coupling and/or uncoupling mechanisms for carrying out the sampling movement and/or for remagazining are also basically possible.

The openings designated in the figures with the reference number 176 on the outer periphery and on the inner periphery of the annular analytical magazine 110 are preferably closed with a sealing film, which can be pierced on the inside by the actuator rod 152 and on the outside by the microsampler 132.

In the oblique perspective top view in FIG. 2A, the rotation between the magazine halves 172 and 174 by half a unit is clearly seen. The test element windows 168, functioning as measuring windows, are shown open. Open measuring windows of this kind are in particular once again of advantage in connection with a test chemistry 142 that is stable against environmental effects.

The double arrangement of the magazine halves 172, 174 can be seen in the sectional view shown in FIG. 2C. Through the rotation of the two magazine halves 172, 174 by half a unit, the microsampler 132 can be seen in different positions with respect to the magazine axis. This arrangement once again makes it possible for the chambers 126 to be nested in one another on both sides of the disk, so that despite the small thickness of the disk, the resultant wall thicknesses between the chambers are sufficiently large functionally or from production considerations.

The chamber 126 shown at the bottom of FIG. 2C is for example in the application position 154 (cf. FIG. 4). In this view, the microsampler 132 in this chamber 126, in the application position 154, is at least partially pushed out of the chamber 126. The actuator rod 152 of an actuator 148, which brings this about, is not shown in the figure. The exploded view in FIG. 2D shows a preferred construction of the analytical magazine 110. It can be seen that the housing 122 essentially comprises three components, which for example, as noted above, can be welded together. Thus, the housing 122 comprises an upper window ring 178, which is arranged in a topmost partial level, and a lower window ring 180, which is arranged in a bottommost partial level. In a middle level, a microlancet ring 182 is arranged, in which chambers 126 for 2×25 microsamplers 132 or microlancets are arranged. These are accommodated, offset relative to one another, in each case on the top and underside of the microlancet ring 182. The elements 178, 180 and 182 can for example be designed as plastic components, for example as injection molded components, for example from one or more thermoplastics.

Contiguous with the microlancet ring 182, above or below in each case in further levels between microlancet ring 182 and the window rings 178, 180, there is in each case an identical chemistry ring 184. These chemistry rings 184 can for example have a carrier film, for example a thin plastic film, which is covered, on the side facing the chambers 126, with the test chemistry 142. The chemistry ring 184 thus forms a continuous test field 144 for all chambers 126 of a level of aids 118, 120, wherein the regions of this test field 144 facing the chambers 126 in each case form individual test fields 144 and therefore partial aids 130 of an analytical aid 128.

In order to transfer the sample from the capillary element 136 of the microsamplers 132 (not shown in the figures) to the test chemistry 142 of the test fields 144 in the chambers 126, once again, similarly to the representation in FIG. 4, a pressing mechanism can be provided. This pressing can for example once again take place through a separate pressing opening. However, it is preferable to effect the pressing in such a way that it takes place from the direction of the test element window 168, thus from the same side from which the measurement is also performed. A small thickness of the carrier film of the chemistry rings 184 makes it possible to press this membrane, clamped in its test element window 168, with a small force onto the microsampler 132 located in its chamber 126, so that contact occurs between the collected sample and the test chemistry 142.

The analytical magazine 110 is closed against the outside by the two window rings 178 and 180, which for example are of essentially identical design. However, additional sealing elements can also be provided. For example, sealing films can be applied on the outer and on the inner periphery, which seal the chamber openings 176 (see FIG. 2A). These are not shown in the figures.

The arrangement according to FIGS. 2A to 2D has in particular the advantage of simple production of the various elements of the housing 122. Both the microlancet ring 182 and the window rings 178, 180 can be produced as simple injection moldings, which can be made in large numbers and with high constancy. The chemistry rings 184 can for example be punched out of a readily available coating film. All rings can for example be centered, aligned and mounted on a central axis.

The individual ring elements of the housing 122 are preferably designed in such a way that they can be joined together with ordinary production methods, producing the smallest possible gaps. In particular, once again gap widths can be produced that are no larger than 10 µm, gaps below the stated diameter or the stated width are characterized by impermeability to microbes and therefore at least largely exclude cross-contamination between used and unused chambers 126 or microsamplers 132. Typical joining techniques such as gluing, ultrasonic welding, laser welding, cold calking or similar techniques are basically known from the prior art and can also be used within the scope of the present invention.

Furthermore, additional auxiliary structures can also be provided on the magazine parts of the housing 122, if they are of advantage for the particular joining technique.

Figure 3:
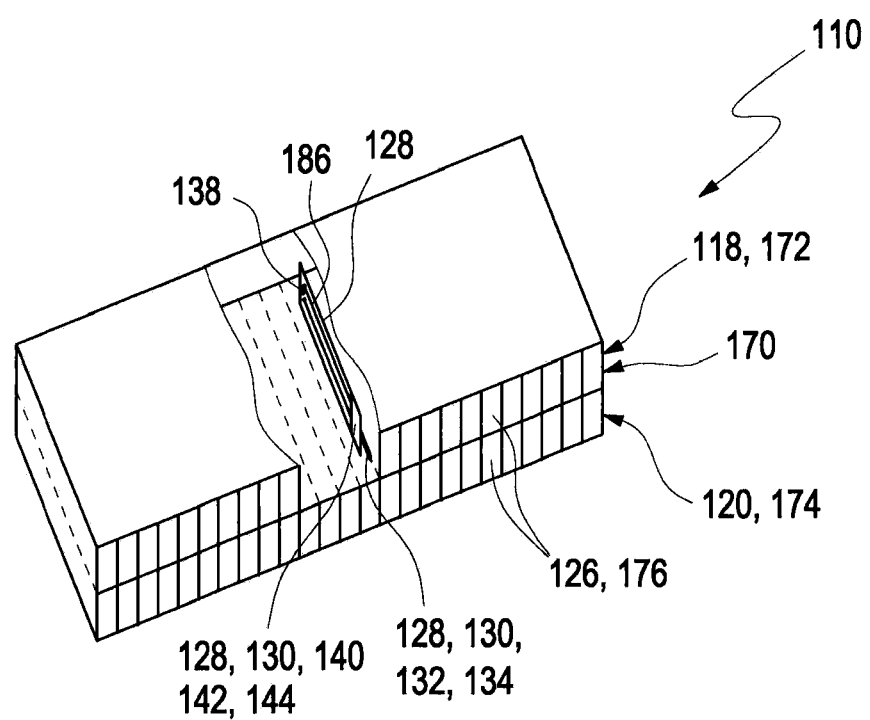
FIG. 3 shows an example of implementation of a linear analytical magazine.

FIG. 3 shows a third example of implementation of an analytical magazine 110, which can once again be used for example in an analytical system of a similar design to the analytical system 114 shown in FIG. 4. The analytical magazine 110 shown here in perspective view is a linear reversing magazine.

The embodiments presented above have essentially been described with reference to analytical aids 128 with optical test chemistry 142. However, other detection methods can also be used, alternatively or additionally to optical evaluation. Thus, the analytical magazine 110 shown in FIG. 3 can for example be used for analytical aids 128, which are evaluated by an electrochemical measuring technique. The optical evaluation and therefore the test element window 168 can therefore be omitted.

In their turn, the analytical aids 128 comprise microsamplers 132 with lancets 134, which are opposite the forward-facing chamber openings 176 in FIG. 3. For example, these microsamplers 132 are arranged on strip-shaped carriers. A capillary element 136 of the microsamplers 132 can transfer the blood sample to test elements 140 with a test chemistry 142 in the form of test fields 144, which can be arranged via electrical contacts 186, for example on an end of the strip-shaped analytical aids 128 opposite the lancet 134.

A coupling mechanism, which is coupled to coupling elements 138 of the analytical aids 128 that are not shown in greater detail in FIG. 3, in order to bring about the sampling movement and/or the remagazining, can also make an electrical connection to the analytical aid 128. Alternatively, additional elements can also be provided for making these electrical connections. A current on the electrochemical contacts of the test elements 140 can be evaluated via the electrical coupling. The measuring system 158 in FIG. 4 can for example be set up for such measurements. Electrochemical measurements of this kind are known from the prior art, for example the aforementioned prior art, and will not be examined more closely here. For example, an analytical aid 128 is shown in FIG. 3 in the form of an electrochemical microsampler in vertical orientation in the analytical magazine 110. However, other arrangements are also basically possible.

The embodiment in FIG. 3 shows, moreover, that it is not absolutely essential to have an offset between the chambers 126 in the upper and the lower magazine half 172, 174. In this embodiment, for example, both magazine halves 172, 174 are designed with mirror symmetry to one another. In particular this has the advantage that magazine positioning can for example take place purely by means of the housing 122 of the analytical magazine 110 and that for example additional positioning aids can also be omitted.

Turning of the analytical magazine 110, i.e. a change of orientation, for changing the magazine half 172, 174 used in each case, can take place in various ways. The arrangement of the analytical aids 128 in the chambers 126 can be adapted to this particular type of change of orientation or turning. For example, in both magazine halves 172, 174 or in both levels of aids 118, 120, the analytical aids 128 can have the same orientation, for example with a lancet 134 pointing to the front chamber opening 176 in FIG. 3. In this case turning takes place about an axis that is oriented parallel to the analytical aids 128 and parallel to the levels of aids 118, 120, for example an axis perpendicular to the narrow front side in FIG. 3. The analytical magazine 110 can therefore be turned round on a narrow edge.

Alternatively, the analytical aids 128 can also be arranged differently in the magazine halves 172, 174, for example with the lancets 134 in the second magazine half 174 pointing backwards in FIG. 3. In this case, when it is turned round, the analytical magazine 110 can for example be rotated about an axis running perpendicular to the analytical aids 128 and parallel to the levels of aids 118, 120, for example an axis running parallel to the longitudinal extension of the linear reversing magazine.

An analytical system 114, which interacts with the analytical magazine 110 according to FIG. 3, can basically be of similar design to that shown in FIG. 4. In particular, once again actuators 148 can optionally be provided with one or more actuator rods 152 and/or other types of coupling elements, which can be coupled to the analytical aids 128. For example, once again an application position 154 can be provided, in which the coupling takes place. By means of these actuators 148, once again a sampling movement can take place, including a corresponding remagazining. Correspondingly, the analytical aids 128 can once again comprise coupling elements 138, for example once again pilot holes, loops or similar, to which the actuator 148 and/or an actuator rod 152 of the actuator 148 can be coupled mechanically. As described above, the mechanical coupling can also optionally be combined with an electrical coupling.

LIST OF REFERENCE SYMBOLS 110 analytical magazine
112 housing (system)
114 analytical system
116 finger opening
118 1st level of aids
120 2nd level of aids
122 housing (magazine)
124 central opening
126 chamber
128 analytical aids
130 partial aids
132 microsampler
134 lancet
136 capillary element
138 coupling element
140 test element
142 test chemistry
144 test field
146 positioning device
148 actuator
150 actuator
152 actuator rod
154 application position
156 actuator rod
158 measuring system
160 control system
162 interface
164 indicating element
166 orientation sensor
168 test element window
170 application plane
172 first magazine half
174 second magazine half
176 chamber openings
178 upper window ring
180 lower window ring
182 microlancet ring
184 chemistry ring
186 electrical contacts

What is claimed is:

1. An analytical magazine comprising at least two chambers, in which analytical aids can be accommodated, wherein the analytical aids are accommodated in at least one of the chambers, wherein the analytical aids in each case comprise at least one microsampler for making at least one opening in a test subject's skin and at least one test element with at least one test chemistry for detecting at least one analyte in a body fluid or other liquid sample, wherein the test chemistry is at least largely stable against moisture, wherein the stability is such that when stored at 32° C., a relative humidity of the air of 85% at normal pressure for a period of three weeks an activity of the test chemistry of the analytical aid decreases by less than 50%, wherein the chambers are designed so that they are separate from one another, in such a way that an exchange of moisture between the chambers is possible, wherein the chambers have chamber walls, wherein gaps or other openings with an opening width of not more than 20 micrometers are provided in the chamber walls, which on the one hand permit exchange of air humidity between the chambers, but which as a rule hold back coarser contaminants or microbes, wherein the analytical magazine is arranged for remagazining the analytical aids in at least one of the chambers after use.

2. The analytical magazine according to claim 1, wherein the analytical magazine has a housing, wherein the housing has a wall thickness of not more than 1.2 mm.

3. The analytical magazine according to claim 1, wherein the analytical magazine is of drying agent-free design.

4. The analytical magazine according to claim 1, wherein the analytical magazine has a housing with at least two parts, wherein the at least two parts are joined together by a laser welding process, wherein at least one weld seam is provided with a weld seam width of max. 0.5 mm.

5. The analytical magazine according to claim 1, wherein the analytical magazine has a housing, wherein the housing has a material selected from the following materials: a polycarbonate; an acrylonitrile-butadiene-styrene; a cyclo-olefin copolymer; a polymethylmethacrylate; a polystyrene; and a polyethylene terephthalate.

6. The analytical magazine according to claim 1, wherein the analytical magazine is arranged to be accommodated in at least two orientations in an analytical system, wherein the analytical magazine is arranged to supply, in the orientations, in each case a plurality of analytical aids to the analytical system, wherein by means of the analytical aids at least one sampling movement can be executed, wherein the analytical aids comprise at least one transfer element for one or both of receiving a sample of a body fluid and transferring the sample, wherein the analytical magazine is arranged to make a remagazining of the analytical aids possible, wherein the analytical magazine is arranged to hold the analytical aids in place in the chambers after remagazining, wherein the analytical magazine comprises at least two partial magazines, wherein each of the partial magazines comprises a plurality of similar analytical aids.

* * * * *